United States Patent
Kuzma et al.

(10) Patent No.: US 7,923,442 B2
(45) Date of Patent: Apr. 12, 2011

(54) GLUTATHIONE PEROXIDASE MIMETICS AND USES THEREOF

(75) Inventors: Dusan Kuzma, Calgary (CA); Thomas G. Back, Calgary (CA); Noah Berkowitz, New Rochelle, NY (US)

(73) Assignee: UTI Limited Partnership, Calgary (CA)

(*) Notice: Subject to any disclaimer, the term of this patent is extended or adjusted under 35 U.S.C. 154(b) by 650 days.

(21) Appl. No.: 11/543,994

(22) Filed: Oct. 6, 2006

(65) Prior Publication Data

US 2007/0123501 A1    May 31, 2007

Related U.S. Application Data

(60) Provisional application No. 60/723,930, filed on Oct. 6, 2005.

(51) Int. Cl.
*A61K 31/33* (2006.01)
*C07D 293/00* (2006.01)
*C07D 329/00* (2006.01)

(52) U.S. Cl. .......................................... 514/183; 540/1
(58) Field of Classification Search ................ 514/183; 540/1

See application file for complete search history.

(56) References Cited

OTHER PUBLICATIONS

Malmsten et al. (CAS Accession No. 1971:492788).*
Mlochowski et al. (CAS Accession No. 1981:192022).*
Nakashima et al. "Optically Active Seleninate Esters: Isolation, Absolute Configuration, Racemization Mechanism, and Transformation into Chiral Selenoxide" Journal of Organic Chemistry, 2005, vol. 70, No. 13, pp. 5020-5027.*

* cited by examiner

*Primary Examiner* — Joseph R Kosack
(74) *Attorney, Agent, or Firm* — Fulbright & Jaworski

(57) ABSTRACT

This invention relates to novel organoselenium and tellurium compounds, processes of producing the same and methods of use thereof. The compounds function as mimetics for the catalyst selenoenzyme glutathione peroxidase, which protects cells from oxidative stress.

6 Claims, 5 Drawing Sheets

GLUTATHIONE PEROXIDASE MIMETICS AND USES THEREOF

CROSS-REFERENCE TO RELATED APPLICATION

This application claims priority to U.S. Ser. No. 60/723,930, filed Oct. 6, 2005, and is incorporated herein by reference in its entirety.

FIELD OF THE INVENTION

This invention relates to novel organoselenium and tellurium compounds, their preparation and methods of use thereof. The compounds behave as mimetics of selenoenzyme glutathione peroxidase, which protects cells from oxidative stress.

BACKGROUND OF THE INVENTION

Oxidative stress is imposed on cells as a result of one of three factors: 1) an increase in oxidant generation, 2) a decrease in antioxidant protection, or 3) a failure to repair oxidative damage. Cell damage is induced by reactive oxygen species (ROS). ROS are either free radicals, reactive anions containing oxygen atoms, or molecules containing oxygen atoms that can either produce free radicals or are chemically activated by them. Examples are hydroxyl radical, superoxide, hydrogen peroxide, and peroxynitrite. The main source of ROS in vivo is aerobic respiration, although ROS are also produced by peroxisomal β-oxidation of fatty acids, microsomal cytochrome P450 metabolism of xenobiotic compounds, stimulation of phagocytosis by pathogens or lipopolysaccharides, arginine metabolism, and tissue specific enzymes. Under normal conditions, ROS are cleared from the cell by the action of superoxide dismutase (SOD), catalase, or glutathione (GSH) peroxidase. The main damage to cells results from the ROS-induced alteration of macromolecules such as polyunsaturated fatty acids in membrane lipids, essential proteins, and DNA. Additionally, oxidative stress and ROS have been implicated in disease states, such as Alzheimer's disease, Parkinson's disease, cancer, aging and diabetes.

The formation of peroxide byproducts during the course of normal aerobic metabolism contributes to oxidative stress in living organisms. Peroxides, as well as free radicals derived from them, have been implicated in a variety of degenerative processes and diseases, including inflammation, cardiovascular disease, mutagenesis and cancer, dementia and the aging process. Fortunately, oxidative stress is mitigated by dietary antioxidants, as well as by endogenous enzymes that catalyze the destruction of peroxides and other reactive oxygen species. The latter include glutathione peroxidase (GPx), which promotes the reduction of peroxides with the stoichiometric reductant glutathione (GSH), a tripeptide thiol that is ubiquitous in the cells of higher organisms.

Despite recent therapeutic advances, cardiovascular disease continues to be the leading cause of death among subjects with diabetes. Diabetes-related heart disease makes up the majority of the cardiovascular morbidity and mortality and this pathology results from synergistic interaction amongst various overlapping mechanisms. Diabetes-related heart disease is characterized by a propensity to develop premature, diffuse atherosclerotic disease, structural and functional abnormalities of the microvasculature, autonomic dysfunction and intrinsic myocardial dysfunction (the so-called diabetic 'cardiomyopathy', a reversible cardiomyopathy in diabetics that occurs in the absence of coronary atherosclerosis), all of which are exacerbated by hypertension and diabetic nephropathy. As far as the probability of the occurrence of an infarction is concerned, the risk for a diabetic is the same as that for a non-diabetic with a previous infarction.

SUMMARY OF THE INVENTION

In a first embodiment, a compound of formula 1 is provided:

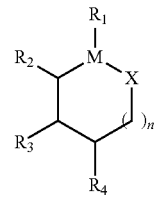

1 wherein,
the compound of formula 1 is a ring; and
X is O or NH
M is Se or Te
n is 0-2
$R_1$ is oxygen; and
  forms an oxo complex with M; or
  $R_1$ is oxygen or NH; and
    forms together with the metal, a 4-7 membered ring, which optionally is substituted by an oxo or amino group; or
    forms together with the metal, a first 4-7 membered ring, which is optionally substituted by an oxo or amino group, wherein said first ring is fused with a second 4-7 membered ring, wherein said second 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl; and $R_2$, $R_3$ and $R_4$ are independently hydrogen, alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl; or $R_2$, $R_3$ or R4 together with the organometallic ring to which two of the substituents are attached, form a fused 4-7 membered ring system wherein said 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl.

In another embodiment, compounds of formula 3 are provided:

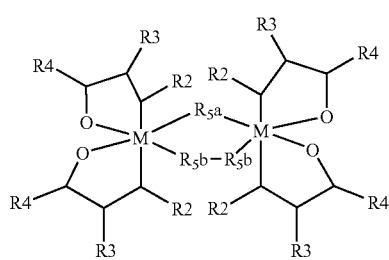

3 wherein,
M is Se or Te
$R_2$, $R_3$ or $R_4$ are independently hydrogen, alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl; or $R_2$, $R_3$ or $R_4$ together with the organometallic ring to which two of the substituents are attached, is a fused 4-7 membered ring system, wherein said 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl; and
$R_{5a}$ or $R_{5b}$ is one or more oxygen, carbon, or nitrogen atoms and forms a neutral complex with the chalcogen.

In another embodiment, a composition or pharmaceutical composition is provided comprising a compound of formula 1 or formula 3, and a suitable carrier or diluent.

In another embodiment, methods are provided for reducing peroxides in a cell, the method comprising contacting the cell with a compound of formula 1 or 3, wherein the compound reduces peroxides in said cell via contacting said compound with a peroxide molecule.

In yet another embodiment, a method is provided for reducing the incidence of oxidative stress, inhibiting suppressing, or diminishing oxidative stress in a subject, the method comprising contacting peroxides with a compound of formula 1 or formula 3.

In still another embodiment, a method is provided for reducing the incidence of oxidative stress, inhibiting suppressing, or diminishing oxidative stress in a subject, the method comprising contacting peroxides with a compound of formula 1 or 3.

In yet a further embodiment, a method is provided for treating, reducing incidence of vascular complication, inhibiting, suppressing or diminishing a vascular complication in a subject, comprising administering to said subject an effective amount of a compound of formula 1 or formula 3, thereby reducing oxidative stress in said subject. In another embodiment, the vascular complication is a cardiovascular complication. In another embodiment, the cardiovascular complication is myocardial infarct or ischemia-reperfusion injury following myocardial infarct. In another embodiment, the vascular complication is microvascular complication or macrovascular complication. In another embodiment, the macrovascular complication is a chronic heart failure, a cardiovascular death, a stroke, a myocardial infarction, a coronary angioplasty associated restenosis, a myocardial ischemia or a combination thereof. In another embodiment, the microvascular complication is diabetic neuropathy, diabetic nephropathy or diabetic retinopathy.

In still another embodiment, the subject is diabetic. In a further embodiment, the diabetic subject has a haptoglobin-2 allele.

DETAILED DESCRIPTION OF THE PRESENT INVENTION

Figure 1:
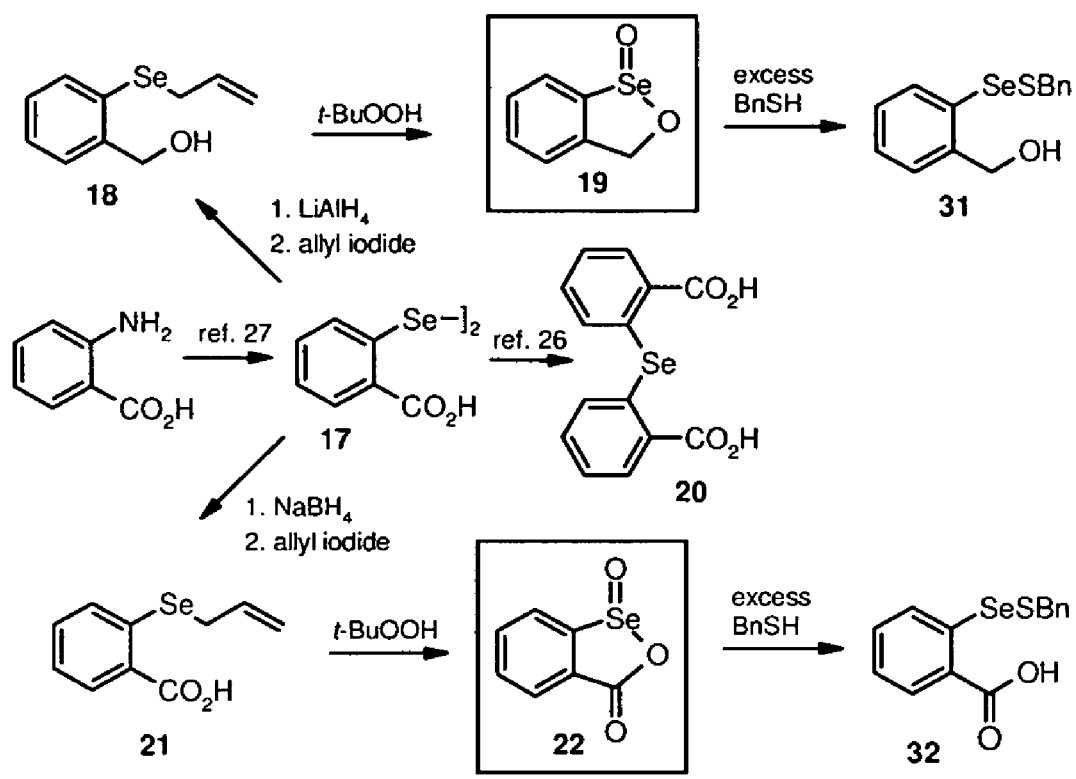
FIG. 1 is a synthetic scheme for the preparation of compounds 19 and 22.

In the following detailed description, numerous specific details are set forth in order to provide a thorough understanding of the invention. However, it will be understood by those skilled in the art that the present invention may be practiced without these specific details. In other instances, well-known methods, procedures, and components have not been described in detail so as not to obscure the present invention.

In one embodiment, a compound of formula 1 is provided:

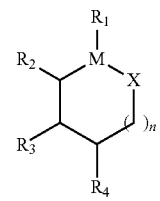

1 wherein,
the compound of formula 1 is a ring; and
X is O or NH
M is Se or Te
n is 0-2
$R_1$ is oxygen; and
  forms an oxo complex with M; or
$R_1$ is oxygen or NH; and
  forms together with the metal, a 4-7 membered ring, which optionally is substituted by an oxo or amino group; or
  forms together with the metal, a first 4-7 membered ring, which is optionally substituted by an oxo or amino group, wherein said first ring is fused with a second 4-7 membered ring, wherein said second 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl; and
$R_2$, $R_3$ and $R_4$ are independently hydrogen, alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl; or $R_2$, $R_3$ or $R_4$ together with the organometallic ring to which two of the substituents are attached, form a fused 4-7 membered ring system wherein said 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl.

In certain embodiments, $R_4$ is not an alkyl. In other embodiments, wherein if $R_2$, $R_3$ and $R_4$ are hydrogens and $R_1$ forms an oxo complex with M, n is 0 then M is Te. In other embodiment, if $R_2$, $R_3$ and $R_4$ are hydrogens and $R_1$ is an oxygen that forms together with the metal an unsubstituted, saturated, 5 membered ring, n is 0 then M is Te. In other embodiments, if $R_1$ is an oxo group, and n is 0, $R_2$ and $R_3$ form together with the organometallic ring a fused benzene ring, $R_4$ is hydrogen, then M is Se. In other embodiments, if $R_4$ is an oxo group, and $R_2$ and $R_3$ form together with the organometallic ring a fused benzene ring, $R_1$ is oxygen, n is 0 and forms together with the metal a first 5 membered ring, substituted by an oxo group α to $R_1$, and said ring is fused to a second benzene ring, then M is Te.

In one embodiment, a 4-7 membered ring group refers to a saturated cyclic ring. In another embodiment the 4-7 membered ring group refers to an unsaturated cyclic ring. In another embodiment the 4-7 membered ring group refers to a heterocyclic unsaturated cyclic ring. In another embodiment the 4-7 membered ring group refers to a heterocyclic saturated cyclic ring. In one embodiment the 4-7 membered ring is unsubstituted. In one embodiment, the ring is substituted by one or more of the following: alkyl, alkoxy, nitro, aryl, cyano, hydroxy, amino, halogen, oxo, carboxy, thio, thioalkyl, or —NH(C=O)$R^A$, —C(=O)$NR^AR^B$, —$NR^AR^B$ or —$SO_2R$ where $R^A$ and $R^B$ are independently H, alkyl or aryl.

In one embodiment, substituent groups may be attached via single or double bonds, as appropriate, as will be appreciated by one skilled in the art.

According to embodiments herein, the term alkyl as used throughout the specification and claims may include both "unsubstituted alkyls" and/or "substituted alkyls", the latter of which may refer to alkyl moieties having substituents replacing a hydrogen on one or more carbons of the hydrocarbon backbone. In another embodiment, such substituents may include, for example, a halogen, a hydroxyl, an alkoxyl, a silyloxy, a carbonyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain may themselves be substituted, if appropriate. For instance, the substituents of a substituted alkyl may include substituted and unsubstituted forms of amines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, and —CN. Of course other substituents may be applied. In another embodiment, cycloalkyls may be further substituted with alkyls, alkenyls, alkoxys, thioalkyls, aminoalkyls, carbonyl-substituted alkyls, $CF_3$, and CN. Of course other substituents may be applied.

The term "alkyl", as used herein, includes both saturated and unsaturated, straight chain (i.e., unbranched) or branched aliphatic hydrocarbons as defined by IUPAC, which are optionally substituted with one or more functional groups, and is intended to include optionally substituted alkyl, alkenyl and alkynyl moieties. Thus, as used herein, the term "alkyl" includes straight and branched alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. In certain embodiments, as used herein, "lower alkyl" is used to indicate those alkyl groups (substituted, unsubstituted, branched or unbranched) having about 1-6 carbon atoms.

In certain embodiments, the alkyl, alkenyl and alkynyl groups employed in the invention contain 1-20; 2-20; 3-20; 4-20; 5-20; 6-20; 7-20 or 8-20 aliphatic carbon atoms. In certain other embodiments, the alkyl, alkenyl, and alkynyl groups employed in the invention contain 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl, alkenyl, and alkynyl groups employed in the invention contain 1-6; 2-6; 3-6; 4-6 or 5-6 aliphatic carbon atoms. In yet other embodiments, the alkyl, alkenyl, and alkynyl groups employed in the invention contain 1-4; 24 or 3-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

In general, the term "aryl" refers to aromatic moieties, as described above, excluding those attached via an aliphatic (e.g., alkyl) or heteroaliphatic (e.g., heteroalkyl) moiety. In certain embodiments of the present invention, "aryl" refers to a mono- or bicyclic carbocyclic ring system having one or two rings satisfying the Huckel rule for aromaticity, including, but not limited to, phenyl, naphthyl, tetrahydronaphthyl, indanyl, indenyl and the like.

The term "alkoxy", as used herein refers to a saturated (i.e., O-alkyl) or unsaturated (i.e., O-alkenyl and O-alkynyl) group attached to the parent molecular moiety through an oxygen atom. In certain embodiments, the alkyl group contains 1-20; 2-20; 3-20; 4-20; 5-20; 6-20; 7-20 or 8-20 aliphatic carbon atoms. In certain other embodiments, the alkyl group contains 1-10; 2-10; 3-10; 4-10; 5-10; 6-10; 7-10 or 8-10 aliphatic carbon atoms. In yet other embodiments, the alkyl, alkenyl, and alkynyl groups employed in the invention contain 1-8; 2-8; 3-8; 4-8; 5-8; 6-20 or 7-8 aliphatic carbon atoms. In still other embodiments, the alkyl group contains 1-6; 2-6; 3-6; 4-6 or 5-6 aliphatic carbon atoms. In yet other embodiments, the alkyl group contains 1-4; 2-4 or 3-4 aliphatic carbon atoms. Examples of alkoxy, include but are not limited to, methoxy, ethoxy, propoxy, isopropoxy, n-butoxy, i-butoxy, sec-butoxy, tert-butoxy, neopentoxy, n-hexoxy and the like.

The term "thioalkyl" as used herein refers to a saturated (i.e., S-alkyl) or unsaturated (i.e., S-alkenyl and S-alkynyl) group attached to the parent molecular moiety through a sulfur atom. In certain embodiments, the alkyl group contains 1-20 aliphatic carbon atoms. In certain other embodiments, the alkyl group contains 1-10 aliphatic carbon atoms. In yet other embodiments, the alkyl, alkenyl, and alkynyl groups employed in the invention contain 1-8 aliphatic carbon atoms. In still other embodiments, the alkyl group contains 1-6 aliphatic carbon atoms. In yet other embodiments, the alkyl group contains 1-4 aliphatic carbon atoms. Examples of thioalkyl include, but are not limited to, methylthio, ethylthio, propylthio, isopropylthio, n-butylthio, and the like.

Encompassed with the substituents of the compounds herein include, but are not limited to aliphatic; alicyclic; heteroaliphatic; heterocyclic; aromatic; heteroaromatic; aryl; heteroaryl; alkylaryl; heteroalkylaryl; alkylheteroaryl; heteroalkylheteroaryl; alkoxy; aryloxy; heteroalkoxy; heteroaryloxy; alkylthio; arylthio; heteroalkylthio; heteroarylthio; F; Cl; Br; I; —OH; —$NO_2$; —CN; —$CF_3$; —$CH_2CF_3$; —$CHCl_2$; —$CH_2OH$; —$CH_2CH_2OH$; —$CH_2NH_2$; —$CH_2SO_2CH_3$; —C(=O)$R_x$; —$CO_2(R_x)$; —C(=O)N($R_x$)$_2$; —OC(=O)$R_x$; —$OCO_2R_x$; —OC(=O)N ($R_x$)$_2$; —N($R_x$)$_2$; —$OR_x$; —$SR_x$; —S(O)$R_x$; —S(O)$_2R_x$; —$NR_x$(C=O)$R_x$; —N(R=)CO=R=; —N(R=)S(O)$R_x$); —N($R_x$)C(=O)N($R_x$)$_2$; —S(O)$_2$N($R_x$)$_2$ wherein each occurrence of $R_x$ independently includes, but is not limited to, aliphatic, alicyclic, heteroaliphatic, heterocyclic, aryl, heteroaryl, alkylaryl, alkylheteroaryl, heteroalkylaryl or heteroalkylheteroaryl, wherein any of the aliphatic, alicyclic, heteroaliphatic, heterocyclic, alkylaryl, or alkylheteroaryl substituents described above and herein may be substituted or unsubstituted, branched or unbranched, saturated or unsaturated, and wherein any of the aryl or heteroaryl substituents described above and herein may be substituted or unsubstituted. Additional examples of generally applicable substituents are illustrated by the specific embodiments shown in the Examples that are described herein.

The term "heterocyclic", as used herein, refers to compounds which combine the properties of heteroaliphatic and cyclic compounds and include but are not limited to saturated and unsaturated mono- or polycyclic ring systems having 5-16 atoms wherein at least one ring atom is a heteroatom selected from O, S and N (wherein the nitrogen and sulfur heteroatoms may be optionally be oxidized), wherein the ring systems are optionally substituted with one or more functional groups, as defined herein. In certain embodiments, the term "heterocyclic" refers to a non-aromatic 5-, 6- or 7-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to an aryl or heteroaryl ring. Representative heterocycles include, but are not limited to, pyrrolidinyl, pyrazolinyl, pyrazolidinyl imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The terms "halo" and "halogen" as used herein refer to an atom selected from fluorine, chlorine, bromine and iodine.

The term "amino", as used herein, refers to a primary (—$NH_2$), secondary (—$NHR_x$), tertiary (—$NR_xR_y$) or quaternary (—$N^+R_xR_yR_z$) amine, where $R_x$, $R_y$ and $R_z$ are independently an aliphatic, alicyclic, heteroaliphatic, heterocyclic, aromatic or heteroaromatic moiety, as defined herein. Examples of amino groups include, but are not limited to, methylamino, dimethylamino, ethylamino, diethylamino, diethylaminocarbonyl, methylethylamino, iso-propylamino, piperidino, trimethylamino, and propylamino.

Some of the compounds described herein can comprise one or more asymmetric centers, and thus can exist in various isomeric forms, e.g., stereoisomers and/or diastereomers. Thus, compounds and pharmaceutical compositions thereof may be in the form of an individual enantiomer, diastereomer or geometric isomer, or may be in the form of a mixture of stereoisomers. In certain embodiments, the compounds are enantiopure compounds. In certain other embodiments, mixtures of stereoisomers or diastereomers are provided.

Furthermore, certain compounds as described herein may have one or more double bonds that can exist as either the Z or E isomer. In other embodiments, compounds are provided as individual isomers substantially free of other isomers and alternatively, as mixtures of various isomers, e.g., racemic mixtures of stereoisomers. Other embodiments include pharmaceutically acceptable derivatives of these compounds and compositions comprising one or more compounds herein and one or more pharmaceutically acceptable excipients or additives.

Compounds may be prepared by crystallization under different conditions and may exist as one or a combination of polymorphs. For example, different polymorphs may be identified and/or prepared using different solvents, or different mixtures of solvents for recrystallization; by performing crystallizations at different temperatures; or by using various modes of cooling, ranging from very fast to very slow cooling during crystallizations. Polymorphs may also be obtained by heating or melting the compound followed by gradual or fast cooling. The presence of polymorphs may be determined by solid probe NMR spectroscopy, IR spectroscopy, differential scanning calorimetry, powder X-ray diffractogram and/or other techniques. Thus, compounds embodied herein further include their derivatives, their tautomeric forms, their stereoisomers, their polymorphs, their pharmaceutically acceptable salts, their pharmaceutically acceptable solvates and pharmaceutically acceptable compositions containing them.

In another embodiment, a compound of formula 2 is provided, wherein M, $R_1$ and $R_4$ are as described above.

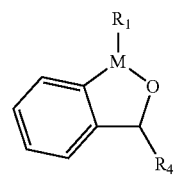

2

In another embodiment, a compound represented by the compound of formula 4 is provided:

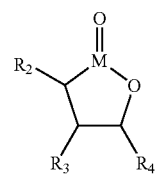

4 wherein, M, $R_2$, $R_3$ and $R_4$ are as described above.

In another embodiment, a compound represented by the compound of formula 5 is provided:

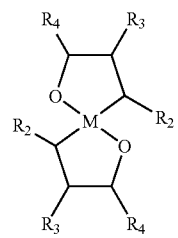

5 wherein, M, $R_2$, $R_3$ and $R_4$ are as described above.

In another embodiment, a compound represented by the compound of formula 6 is provided:

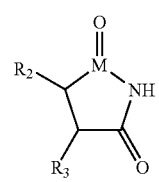

6 wherein, M, $R_2$, and $R_3$ are as described above.

In another embodiment, a compound, represented by the compound of formula 7 is provided:

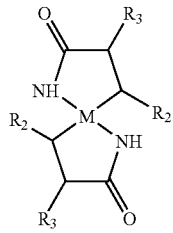

7 wherein, M, $R_2$, and $R_3$ are as described above.

In another embodiment, a compound, represented by the compound of formula 8 is provided:

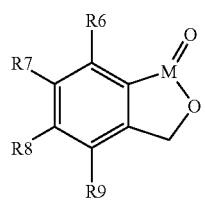

8 wherein, M is as described above each of R6, R7, R8 and R9 is independently alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl.

In another embodiment, a compound, represented by the compound of formula 9 is provided:

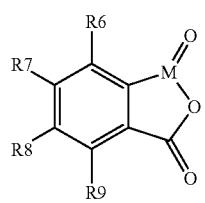

9 wherein, M is as described above and each of R6, R7, R8 and R9 is independently alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl.

In another embodiment, a compound, represented by the compound of formula 10 is provided:

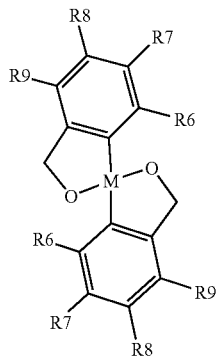

10 wherein, M is as described above and each of R6, R7, R8 and R9 is independently alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl.

In another embodiment, a compound, represented by the compound of formula 11 is provided:

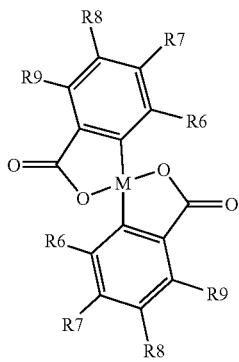

11 wherein, M is as described above and each of R6, R7, R8 and R9 is independently alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl.

In another embodiment, a compound of formula 22 is provided:

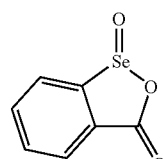

22

In another embodiment, a compound of formula 24 is provided:

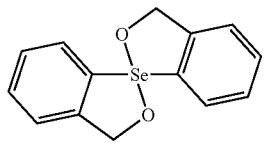

24

In another embodiment, a compound of formula 27 is provided:

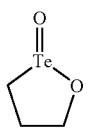

27

In another embodiment, a compound of formula 29 is provided:

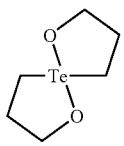

29

In another embodiment, a compound of formula 12 is provided:

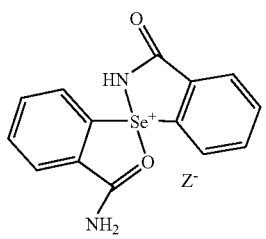

12 wherein $Z^-$ is $Cl^-$ or $^-OH$.

In another embodiment, the following compounds are provided.

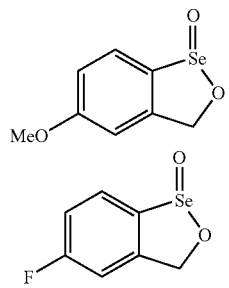

-continued

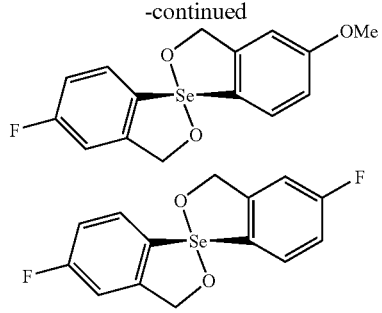

In another embodiment, compounds of formula 3 are provided:

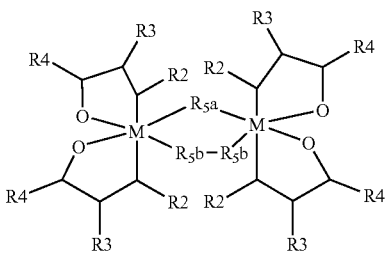

3 wherein,
  M is Se or Te;
  $R_2$, $R_3$ or $R_4$ are independently hydrogen, alkyl, alkoxy, nitro, aryl, cyano, hydroxy, amino, halogen, oxo, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl; or $R_2$, $R_3$ or $R_4$ together with the organometallic ring to which two of the substituents is attached, is a fused 4-7 membered ring system, wherein said 4-7 membered ring is optionally substituted by alkyl, alkoxy, nitro, aryl, cyano, hydroxy, amino, halogen, oxo, carboxy, thio, thioalkyl, or —NH(C=O)$R^A$, —(=O)NR$^A$R$^B$, —NR$^A$R$^B$ or —SO$_2$R where $R^A$ and $R^B$ are independently H, alkyl or aryl; and
  $R_{5a}$ or $R_{5b}$ is one or more oxygen, carbon, or nitrogen atoms and forms a neutral complex with the chalcogen.

In another embodiment formula 3 is represented by the compound of formula 33:

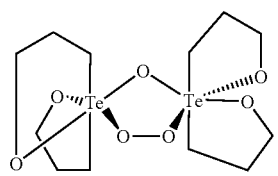

33

The descriptions of substituents such as alkyl, aryl, alkoxy, thioalkyl and the like are as described above. In one embodiment $R_{5a}$ and each of $R_{5b}$ are independently one or more oxygen, carbon, or nitrogen atoms and forms a neutral complex with the chalcogen. In another embodiment, $R_{5a}$ and —$R_{5b}$—$R_{5b}$— are each a bridge between the two chalcogen rings. In another embodiment a bridge is an oxygen based bridge. In another embodiment a bridge is a carbon based bridge. In another embodiment the bridge is an electron based bridge. In another embodiment a bridge is another metal complex bridge. In another embodiment a bridge is a Se bridge. In another embodiment a bridge is a Te bridge. In another embodiment a bridge is a carbonyl based bridge. In another embodiment a bridge is an N based bridge. In another embodiment a bridge is bispyridyl bridge. In another embodiment a bridge is a polymer bridge. In another embodiment a bridge is a carbon based bridge. In another embodiment a bridge is a conjugated carbon bridge or unconjugated carbon bridge. In another embodiment a bridge is silicon based bridge. In another embodiment a bridge is a sulfur based bridge. In another embodiment, a bridge comprises of one or more of the atoms described hereinabove, or any combination thereof.

In another embodiment, $R_{5a}$ is —O— (ether bridge), and —$R_{5b}$—$R_{5b}$— is (peroxide bridge).

In another embodiment, compounds of the following formula are provided:

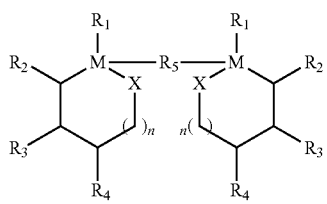

wherein, the compound is composed of at least two rings; and

M is Se or Te $R_1$ is oxygen; and forms an oxo complex with M; or $R_1$ is oxygen or NH; and forms together with the metal, a 4-7 membered ring, which optionally is substituted by an oxo or amino group; or forms together with the metal a first 4-7 membered ring, which is optionally substituted by an oxo or amino group, wherein said first ring is fused with a second 4-7 membered ring, wherein said second 4-7 membered ring is optionally substituted by an alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl;

$R_2$, $R_3$ or $R_4$ are independently hydrogen, alkyl, oxo, amino, or together with the organometallic ring to which two of the substituents are attached, a fused 4-7 membered ring system, wherein said 4-7 membered ring is optionally substituted by alkyl, alkoxy, nitro, aryl, cyano, hydroxy, amino, halogen, oxo, carboxy, thio, thioalkyl, or —NH(C=O)$R^A$, —C(=O)N$R^A R^B$, —N$R^A R^B$ or —SO$_2$R where $R^A$ and $R^B$ are independently H, alkyl or aryl; and $R_5$ is one or more oxygen, carbon, or nitrogen atoms and forms a neutral complex with the chalcogen.

In another embodiment, compounds of the following formula are provided:

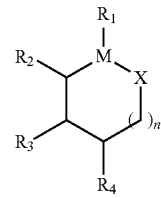

wherein, a compound of formula 1 is a ring; and

X is O or NH

M is Se or Te n is 0-2

$R_1$ is oxygen; and forms an oxo complex with M; or forms together with the metal, a 4-7 membered ring, which optionally is substituted by an oxo group; or forms together with the metal, a first 4-7 membered ring, which is optionally substituted by an oxo group, wherein said first ring is fused with a second 4-7 membered ring, wherein said second 4-7 membered ring is optionally substituted by alkyl, phenyl or halogen;

$R_2$, $R_3$ and $R_4$ are independently hydrogen, alkyl, oxo, or together with the organometalic ring to which two of the substituents are attached, a fused 4-7 membered ring system wherein said 4-7 membered ring is optionally substituted by alkyl, phenyl or halogen.

In one embodiment, a method is provided for reducing peroxides in a cell, the method comprising contacting a cell with a compound described herein; wherein said compound reduces peroxides in said cell via contacting said compound with a peroxide molecule.

In one embodiment, the compounds act as catalysts in reactions involving the reduction of peroxides. In one embodiment, the compounds mimic glutathione peroxidase activity. In another embodiment the catalytic cycle of glutathione peroxidase requires a stoichiometric reductant to be present, which is a thiol such as glutathione (in cells) or benzyl thiol (BnSH) (in the vitro assay described herein).

The term "mimic" refers, in one embodiment to comparable, identical, or superior activity, in the context of conversion, timing, stability or overall performance of the compound, or any combination thereof.

In another embodiment, compounds are provided which can be used as catalysts which reduce peroxides and may be used in reactions which involve glutathione peroxidase reduction of peroxides, intracellularly, or in another embodiment, extracellularly.

Glutathione peroxidase (GPx) is a selenium-containing enzyme that protects cells via its catalytic reduction of peroxides with the thiol, glutathione (GSH). The enzyme has a tetrameric structure, in which each subunit contains a selenocysteine residue.

In another embodiment, glutathione peroxidase, is an important defense mechanism against myocardial ischemia-reperfusion injury, and is markedly decreased in one embodiment, in the cellular environment of diabetes mellitus. In vitro and in vivo studies with GPx mimetics show in one embodiment, that glutathione peroxidase is capable of protecting cells against reactive oxygen species and in another embodiment, inhibiting inflammation via action as an inhibitor of NF-κB activation.

Glutathione peroxidase (GPx) can be found largely in mammals cells, in mitochondrial matrix and cytoplasm. It reacts in one embodiment, with a large number of hydroperoxides (R—OOH). Glutathione peroxidase is of great importance within cellular mechanism for detoxification, since it is able in another embodiment, to reduces, in the same manner, the hydroperoxides from lipidic peroxidation. GPx is distributed extensively in cell, blood, and tissues, and its activity decreases when an organism suffers from diseases such as diabetes. In one embodiment, GPx is involved in many pathological conditions and is one of the most important antioxidant enzymes in living organisms. However, the therapeutic usage of the native GPx is limited because of its instability, its limited availability, and the fact that is extremely difficult to prepare by using genetic engineering techniques because it contains selenocysteine encoded by the stop codon UGA.

In one embodiment GPx have been identified: cellular GPx (cGPx), gastrointestinal GPx, extracellular GPx, and phospholipid hydroperoxide GPx. It reduces hydrogen peroxide as well as a wide range of organic peroxides derived from unsaturated fatty acids, nucleic acids, and other important biomolecules. At peroxide concentrations encountered under physiological conditions and in another embodiment, it is more active than catalase (which has a higher $K_m$ for hydrogen peroxide) and is active against organic peroxides in another embodiment. Thus, cGPx represents a major cellular defense against toxic oxidant species.

Peroxides, including hydrogen peroxide ($H_2O_2$), are one of the main reactive oxygen species (ROS) leading to oxidative stress. $H_2O_2$ is continuously generated by several enzymes (including superoxide dismutase, glucose oxidase, and monoamine oxidase) and must be degraded to prevent oxidative damage. The cytotoxic effect of $H_2O_2$ is thought to be caused by hydroxyl radicals generated from iron-catalyzed reactions, causing subsequent damage to DNA, proteins, and membrane lipids.

A cell undergoing oxidative stress will exhibit in one embodiment phenotypic changes as result of the above. In one embodiment oxidative stress refers in one embodiment to a loss of redox homeostasis (imbalance) with an excess of reactive oxidative species (ROS) by the singular process of oxidation. Both redox and oxidative stress are associated in another embodiment, with an impairment of antioxidant defensive capacity as well as an overproduction of ROS. In another embodiment, the methods and compositions embodied herein are used in the treatment of complications or pathologies resulting from oxidative stress in diabetic subjects.

Catalytic activity of the compounds described herein can be determined via assessing the reduction of tert-butyl hydroxyperoxide and hydrogen peroxide with benzyl thiol for example as described in Example 1, herein. According to this embodiment, catalytic activity was compared by means of reaction half-life ($t_{1/2}$), where the value reflects the time required to oxidize half of the thiol to its disulfide.

The compounds described herein prepared according to the teaching herein may be incorporated into pharmaceutical compositions. The term "pharmaceutical composition", in one embodiment, refers to a "therapeutically effective amount" of the active ingredient, the compounds embodied herein, together with a pharmaceutically acceptable carrier or diluent. The term "therapeutically effective amount" in one embodiment, refers to an amount, which provides a therapeutic effect for a given condition and administration regimen.

In one embodiment, a composition is provided, or in another embodiment, a pharmaceutical composition comprising at least one compound described herein. In another embodiment, compositions and pharmaceutical compositions are provided comprising two or more compounds embodied herein. In another embodiment, compositions are provided comprising at least one compound embodied herein, and an antioxidant, such as BHA (butylated hydroxyanisole), BHT (butylated hydroxytoluene), vitamin E, β carotene, ascorbic acid, propyl gallate, octyl gallate, dodecyl gallate, α tocopherol, γ tocopherol, δ tocopherol or any combination thereof, or others known in the art.

The pharmaceutical compositions containing a compound embodied herein can be administered to a subject by any method known to a person skilled in the art, such as orally, parenterally, paracancerally, transmucosally, transdermally, intramuscularly, intravenously, intradermally, subcutaneously, intraperitoneally, intraventricularly, intracranially, intravaginally by inhalation or intratumorally. Pharmaceutical compositions also comprise solutions for storing, bathing or transporting cells, tissues or organs, for use, for example, during transport between donor and recipient for transplant, or for temporary storage during procedures requiring temporary removal or ex vivo manipulation of cells, tissue or organs.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets, powders, and the like. Suitable liquid oral formulations include solutions, suspensions, dispersions, emulsions, oils and the like. In one embodiment, the compounds embodied herein are formulated in a capsule. In accordance with this embodiment, the compositions herein comprise in addition to the compounds described herein and the inert carrier or diluent, a hard gelatin capsule.

In one embodiment, the term "administering" or "administer" or "administered" refers contact, whether direct or indirect, with a compound embodied herein. In one embodiment, administration can be accomplished in vitro, ex vivo, or in vivo, In one embodiment, administration refers to direct injection at a site, or in another embodiment, parenteral injection, wherein the body conveys the material to the desired site. In one embodiment, administration encompasses ex-vivo or in vitro culture of a cell with a compound described herein, which, in another embodiment, may then be implanted in the subject. In one embodiment, the methods embodied herein encompass administering the compounds to a subject, via any acceptable route.

Further, in another embodiment, the pharmaceutical compositions are administered by intravenous, intra-arterial, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intra-arterial, and are thus formulated in a form suitable for intra-arterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the compounds herein or their physiologically tolerated derivatives such as salts, esters, N-oxides, and the like are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of the compounds a period of time. In a further embodiment, the pharmaceutical compositions are administered intravaginally.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregelatinized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, cyclodextrins, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., cremophor, glycerol, polyethylene glycerol, benzalkonium chloride, benzyl benzoate, cyclodextrins, sobitan esters, stearic acids), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates), and/or adjuvants.

In one embodiment, the pharmaceutical compositions provided herein are controlled release compositions, i.e. compositions in which the compound is released over a period of time after administration. Controlled or sustained release compositions include formulation in lipophilic depots (e.g. fatty acids, waxes, oils). In another embodiment, the composition is an immediate release composition, i.e. a composition in which all of the compound is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

The compositions may also include incorporation of the active material into or onto particulate preparations of polymeric compounds such as polylactic acid, polyglycolic acid, hydrogels, etc, or onto liposomes, microemulsions, micelles, unilamellar or multilamellar vesicles. Such compositions will influence the physical state, solubility, stability, rate of in vivo release, and rate of in vivo clearance.

Also comprehended herein are particulate compositions coated with polymers (e.g. poloxamers or poloxamines) and the compound coupled to antibodies directed against tissue-specific receptors, ligands or antigens or coupled to ligands of tissue-specific receptors.

Also comprehended herein are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981, Cancer Treat Rep. 1981 65:1077-81; Newmark et al., 1982, J. Appl. Biochem. 4:185-189; and Katre et al., 1987, Proc Natl Acad Sci USA 84:1487-91). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the compounds are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the compounds or their physiologically tolerated derivatives such as salts, esters, N-oxides, and the like are converted into a solution, suspension, or emulsion, if desired with the substances customary and suitable for this purpose, for example, solubilizers or other.

In one embodiment, the compounds are used to reduce incidence of, reduce, treat, diminish, prevent or otherwise positively modulate oxidative stress in a cell or tissue.

Oxidative stress refers in one embodiment to a loss of redox homeostasis (imbalance) with an excess of reactive oxidative species (ROS) by the singular process of oxidation. Both redox and oxidative stress are associated in another embodiment, with an impairment of antioxidant defensive capacity as well as an overproduction of ROS.

In one embodiment, oxidative stress is detected by detecting chemical products and intermediates that are artifacts of or associated with oxidative stress by spectroscopic techniques manifested as changes in absorption, fluorescence, IR, NMR and ESR etc., as will be appreciated by one skilled in the art. The effect of the compounds on these phenomena may therefore be readily evaluated.

In one embodiment, a method is provided for reducing incidence of oxidative stress, inhibiting, suppressing or diminishing oxidative stress in a cell of a subject, via contacting a cell undergoing oxidative stress in the subject with a compound embodied herein, or a composition comprising the same.

In one embodiment, methods are provided for reducing incidence of oxidative stress, inhibiting, suppressing or diminishing oxidative stress via contacting a cell undergoing oxidative stress in the subject with a compound of formula 22, or a composition comprising the same.

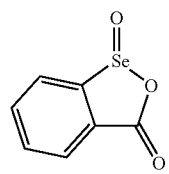

22

In one embodiment, methods are provided for reducing incidence of oxidative stress, inhibiting, suppressing or diminishing oxidative stress via contacting a cell undergoing oxidative stress in the subject with a compound of formula 24, or a composition comprising the same:

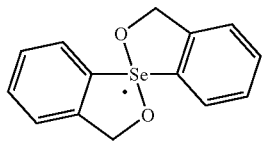

24

In one embodiment, a method is provided for reducing incidence of oxidative stress, inhibiting, suppressing or diminishing oxidative stress via contacting a cell undergoing oxidative stress in the subject with a compound of formula 27, or a composition comprising the same.

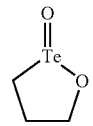

27

In one embodiment, a method is provided for reducing incidence of oxidative stress, inhibiting, suppressing or diminishing oxidative stress via contacting a cell undergoing oxidative stress in the subject with a compound of formula 29, or a composition comprising the same.

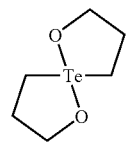

29

In one embodiment, a method is provided for reducing incidence of oxidative stress, inhibiting, suppressing or diminishing oxidative stress via contacting a cell undergoing oxidative stress in the subject with a compound of formula 12, or a composition comprising the same, where $Z^-$ is $Cl^-$ or $^-OH$.

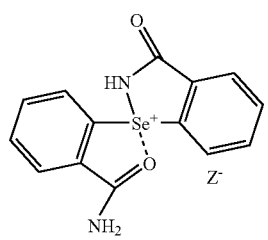

12

In one embodiment, a method is provided for reducing incidence of oxidative stress, inhibiting, suppressing or diminishing oxidative stress via contacting a cell undergoing oxidative stress in the subject with a compound among the four shown below, or a composition comprising the same.

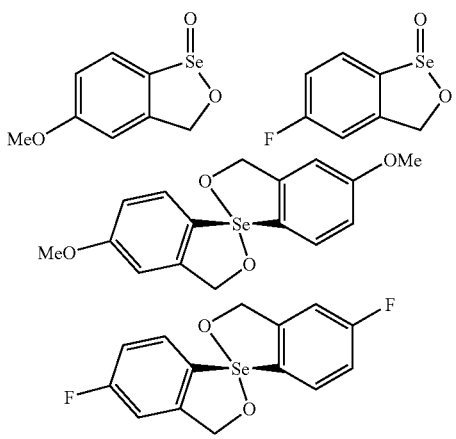

In one embodiment, a method is provided for reducing incidence of oxidative stress, inhibiting, suppressing or diminishing oxidative stress via contacting a cell undergoing oxidative stress in the subject with a compound of formula 33, or a composition comprising the same:

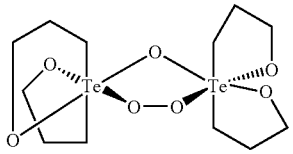

33

In one embodiment, a method is provided for reducing incidence of oxidative stress, inhibiting, suppressing or diminishing diseases associated with oxidative stress by administering a compound described herein, or a composition comprising the same. In another embodiment the diseases associated with oxidative stress are atherosclerosis, neurodegenerative disorders, Alzheimer's disease, cancer, Hepatitis C, viral Hepatitis B, cataractogenesis, ischemia, hepatotoxicity and tumor growth.

In one embodiment a method is provided for treatment of a cardiovascular complication in a subject, comprising administering to said subject an effective amount of a compound embodied herein, thereby reducing oxidative stress in said subject.

In another embodiment, the vascular complication is a macrovascular complication such as chronic heart failure, cardiovascular death, stroke, myocardial infarction, coronary angioplasty associated restenosis, fewer coronary artery collateral blood vessels and myocardial ischemia in other embodiments. In one embodiment, the vascular complication is a microvascular complication, such as diabetic neuropathy, diabetic nephropathy or diabetic retinopathy in other embodiment. In one embodiment, microvascular complications lead to renal failure, or peripheral arterial disease (also known as peripheral vascular disease), or limb amputation in other embodiments.

Microvascular disease may be characterized in one embodiment, by an unevenly distributed thickening (or hyalinization) of the intima of small arterioles, due in another embodiment, to the accumulation of type IV collagen in the basement membrane, or microaneurisyms of the arterioles, which compromises the extent of the maximal arteriolar dilation that can be achieved and impairs the delivery of nutrients and hormones to the tissues, or to remove waste in another embodiment. The vasculature distal to the arterioles may also be affected in one embodiment, such as by increased capillary basement membrane thickening, abnormalities in endothelial metabolism, or via impaired fibrinolysis, also resulting in reduced delivery of nutrients and hormones to the tissues, or waste removal in another embodiment. Microvascular disease results in one embodiment in microvascular diabetic complications, which in another embodiment, are treated by the methods described herein.

In one embodiment, capillary occlusions constitute a characteristic pathologic feature in early diabetic retinopathy, and initiate neovascularization in another embodiment. Microaneurysms, intraretinal microvascular abnormalities and vasodilation are commonly found in early stages of diabetic retinopathy and have been correlated to capillary occlusions. In another embodiment, leukocytes cause capillary obstruction that is involved in diabetic retinopathy. This obstruction is the result of the leukocytes' large cells volume and high cytoplasmic rigidity. Leukocytes can become trapped in capillaries under conditions of reduced perfusion pressure (e.g., caused by vasoconstriction) or in the presence of elevated adhesive stress between leukocytes and the endothelium, endothelial swelling, or narrowing of the capillary lumen by perivascular edema. Examples of leukocytes include granulocytes, lymphocytes, monocytes, neutrophils, eosinophils, and basophils. Elevated adhesive stress results in one embodiment, from release of chemotactic factors, or expression of adhesion molecules on leukocytes or endothelial cells in other embodiments.

According to this aspect and in one embodiment, a method is provided for treating reducing incidence of cardiovascular complication, inhibiting, suppressing or diminishing cardiovascular complications in a subject, comprising reducing oxidative stress in said subject, wherein said subject is diabetic. Likewise, a method is provided for treating such complications in a non-diabetic subject.

Patients having diabetes and having in one embodiment, an additional condition or disease such as cardiovascular disease, or ischemic heart disease, congestive heart failure, congestive heart failure but not having coronary arteriosclerosis, hypertension, diastolic blood pressure abnormalities, microvascular diabetic complications, abnormal left ventricular function, myocardial fibrosis, abnormal cardiac function, pulmonary congestion, small vessel disease, small vessel disease without atherosclerotic cardiovascular disease or luminal narrowing, coagulopathy, cardiac contusion, or having or at risk of having a myocardial infarction in other embodiments, are at particular risk for developing very serious cardiac insufficiencies including death because diabetic cardiomyopathy further adversely affects the subject's heart and cardiovascular system.

Any such subjects may be treated with the compounds and/or methods described herein.

In another embodiment, the cardiovascular complication is a myocardial infarct. In another embodiment, the cardiovascular complication is a result of an ischemia reperfusion injury following myocardial infarct (MI).

In another embodiment the treatment comprises treating, reducing incidence, or alleviating symptoms, eliminating recurrence, preventing recurrence, preventing incidence, improving symptoms, improving prognosis or combination thereof.

In another embodiment the vascular complication is microvascular complication or macrovascular complication. In another embodiment, the macrovascular complication is a chronic heart failure, a cardiovascular death, a stroke, a myocardial infarction, a coronary angioplasty associated restenosis, a myocardial ischemia or a combination thereof. In another embodiment the microvascular complication is diabetic neuropathy, diabetic nephropathy or diabetic retinopathy.

In another embodiment, a method is provided for treating atherosclerosis in a subject, comprising administering to said subject an effective amount of a compound described herein.

In another embodiment, a method is provided for treating ischemia in a subject, comprising administering to said subject an effective amount of a compound described herein.

In one embodiment, administering a compound described herein, or a composition comprising the same, treats, suppresses, inhibits, diminishes, delays, abrogates or otherwise positively modulates a disease, disorder or condition as described herein, or a symptom associated with a disease, disorder or condition as described herein. In one embodiment, the compounds treat oxidative stress associated with a disease, disorder or condition, as described herein, which results in resolution of the disease, disorder or condition. In one embodiment, the compounds treat oxidative stress associated with a disease, disorder or condition, as described herein, which delays progression, alters pathogenesis, diminishes severity, enhances mortality, diminishes morbidity of subjects with regards to the compounds treat oxidative stress associated with a disease, disorder or condition, as described herein.

The term "myocardial infarct" or "MI" refers in another embodiment, to any amount of myocardial necrosis caused by ischemia. In one embodiment, an individual who was formerly diagnosed as having severe, stable or unstable angina pectoris can be diagnosed as having had a small MI. In another embodiment, the term "myocardial infarct" refers to the death of a certain segment of the heart muscle (myocardium), which in one embodiment, is the result of a focal complete blockage in one of the main coronary arteries or a branch thereof. In one embodiment, subjects who were formerly diagnosed as having severe, stable or unstable angina pectoris, are treated according to the methods or in another embodiment with the compositions embodied herein, upon determining these subjects carry the haptoglobin-2 (Hp-2) allele and are diabetic.

The term "ischemia-reperfusion injury" refers in one embodiment to a list of events including: reperfusion arrhythmias, microvascular damage, reversible myocardial mechanical dysfunction, and cell death (due to apoptosis or necrosis). These events may occur in another embodiment, together or separately. Oxidative stress, intracellular calcium overload, neutrophil activation, and excessive intracellular osmotic load explain in one embodiment, the pathogenesis and the functional consequences of the inflammatory injury in the ischemic-reperfused myocardium. In another embodiment, a close relationship exists between reactive oxygen species and the mucosal inflammatory process.

These and other aspect will now be described in greater details by reference to the following non-limiting Examples.

Example 1

Synthesis of an Oxaselenolane Se-Oxide (FIG. 1)

Diselenide 17, selenide 20 and spirodioxyselenurane 25 were prepared by literature procedures. NMR spectra were run in $CDCl_3$ unless otherwise indicated. Chemical shifts for $^{77}Se$ and $^{125}Te$ NMR spectra are reported relative to dimethyl selenide and dimethyl telluride, respectively ($\delta$ 0.00). The spectra were recorded by using diphenyl diselenide in $CDCl_3$ ($\delta$ 463 ppm) or selenium dioxide in $D_2O$ ($\delta$ 1302.6 ppm) for $^{77}Se$ NMR spectra, and diphenyl ditelluride in $CDCl_3$ ($\delta$ 420.8 ppm) for $^{125}Te$ NMR spectra. Benzyl thiol was distilled prior to use and the concentrations of tert-butyl hydroperoxide and hydrogen peroxide were determined by iodometric analysis.

Glassware used in the measurement of catalytic activity (Example 9) was washed only with water followed by acetone, and was flame-dried prior to use. Contamination with traces of detergent or alkali produced abnormal kinetic results.

Allyl (2-hydroxymethyl)phenyl selenide (18). Diselenide 17 (prepared according to Lesser, R.; Weiss, R. Ber. 1913, 2640; ref. 27 in FIG. 1) (1.43 g, 3.57 mmol) in 50 ml of dry THF was added dropwise to a stirred solution of 0.69 g (18 mmol) of lithium aluminum hydride in 20 mL of dry THF at 0° C. After the initial vigorous reaction subsided, the mixture was warmed to room temperature, stirred for 6 h and treated with 0.7 mL (8 mmol) of allyl iodide. Stirring was continued overnight, the mixture was quenched with 100 mL of water, filtered and the residue was washed thoroughly with ether. The filtrate was extracted repeatedly with ether. The combined organic layers were dried and concentrated in vacuo. The crude product was chromatographed (elution with hexanes-ethyl acetate 3:2) to afford 816 mg (50%) of 18 as a yellow oil: IR (neat) 3350 (br), 1028, 750 $cm^{-1}$; $^1H$ NMR (300 MHz) $\delta$ 7.54 (dd, J=7.4, 1.3 Hz, 1H), 7.40 (dd, J=7.4, 1.3 Hz, 1H), 7.31-7.18 (m, 2H), 6.00-5.86 (m, 1H), 4.99-4.92 (m, 2 H), 4.76 (s, 2H), 3.51 (d, J=7.7 Hz, 2H), 2.40 (br s, 1H); $^{13}C$ NMR (75 MHz) $\delta$ 143.0, 134.8, 134.3, 129.7, 128.5, 128.4, 128.0, 117.3, 65.6, 31.1; mass spectrum, m/z (relative intensity) 228 (10, $M^+$), 187 (38), 157 (17), 129 (26), 105 (17), 78 (100). Exact mass calcd for $C_{10}H_{12}O^{80}Se$: 228.005. Found: 228.00600.

Benzo-1,2-oxaselenolane Se-Oxide (19). tert-Butyl hydroperoxide (0.96 mL of 38% aqueous solution, 3.9 mmol) was added to 448 mg (1.97 mmol) of selenide 18 in 15 mL of dichloromethane. The mixture was stirred at room temperature overnight, concentrated in vacuo and chromatographed (elution with 20% methanol-ethyl acetate) to afford 351 mg (88%) of 19 as a white solid: mp 139-140° C. (from ethyl acetate); IR (KBr) 1462, 1260, 966 $cm^{-1}$); $^1H$ NMR (300 MHz) $\delta$ 7.81 (d, J=7.7 Hz, 1H), 7.61-7.47 (m, 3H), 5.97 (d, J=13.8 Hz, H), 5.61 (d, J=13.6 Hz, 1H); $^{13}C$ NMR (75 MHz) $\delta$ 148.3, 143.7, 132.2, 129.3, 125.5, 122.9, 78.6; $^{77}Se$ NMR (76 MHz) $\delta$ 1349.1; mass spectrum, m/z (relative intensity) 202 (30, $M^+$), 106 (74), 78 (100). Exact mass calcd for $C_7H_6O_2^{80}Se$: 201.9533. Found: 201.9540. Analysis calcd for $C_7H_6O_2Se$: C, 41.81; H, 3.01. Found: C, 41.54; H 2.97.

Allyl 2-carboxyphenyl selenide (21). Sodium borohydride (0.59 g, 16 mmol) was added to diselenide 17 (prepared according to Lesser, R.; Weiss, R. Ber. 1913, 2640) (1.24 g, 3.10 mmol) in 60 mL of dry THF. The stirred mixture was cooled to 0° C. and 50 mL of absolute ethanol was added dropwise. The mixture was warmed to room temperature and after 15 min, 1.3 mL (12.4 mmol) of allyl iodide was added. After 1 h, the mixture was acidified with 120 mL of 1 M HCl and extracted with ether. The combined organic phases were washed with water, dried and concentrated in vacuo. The residue was chromatographed (elution with 30% dichloromethane-ethyl acetate) to give 998 mg (67%) of 21 as a white solid: mp 137-138° C. (from benzene-petroleum ether); IR (KBr) 3200-2300 (br), 1660 $cm^{-1}$; $^1H$ NMR (300 MHz) $\delta$ 8.16 (d, J=7.7 Hz, 1H), 7.47-7.43 (m, 2H), 7.29-7.23 (m, 1H), 6.07-5.96 (m, 1H), 5.39 (dd, J=16.9, 1.3 Hz, 1H), 5.15 (d, J=10.0 Hz, 1H), 3.59 (d, J=7.2 Hz, 2H); $^{13}C$ NMR (75 MHz) $\delta$ 172.0, 139.3, 133.4, 133.3, 132.8, 128.3, 127.4, 124.9, 118.5, 28.4; mass spectrum, m/z (relative intensity) 242 (19, $M^+$), 201 (100). Exact mass calcd for $C_{10}H_{10}O_2^{80}Se$: 241.9846. Found: 241.9832. Analysis calcd for $C_{10}H_{10}O_2Se$: C, 49.81; H, 4.18. Found: C, 49.72; H, 3.91.

Benzo-3-oxo-1,2-Oxaselenolane Se-Oxide (22). tert-Butyl hydroperoxide (0.65 mL of 56% aqueous solution, 3.8 mmol) was added to 322 mg (1.33 mmol) of selenide 21 in 40 mL of dichloromethane. The mixture was stirred at room temperature for 14 h, concentrated in vacuo and recrystallized from acetonitrile to provide 212 mg (74%) of 22 as a white solid with mp 226-227° C. (from water); IR (KBr) 1653, 1583, 1276 $cm^{-1}$; $^1H$ NMR (300 MHz, $CD_3OD$) $\delta$ 8.23 (dd, J=7.7, 1.0 Hz, 1H), 8.11 (dd, J=7.4 Hz, 1.3 Hz, 1H), 7.85-7.80 (m, 1H), 7.69-7.65 (m, 1H) NMR (100 MHz, $D_2O$, 340 K) $\delta$ 170.8, 147.8, 134.8, 133.3, 131.6, 130.3, 125.1; $^{77}Se$ NMR (57 MHz, $DMSO-d_6$) $\delta$ 1022.3; mass spectrum, m/z (relative intensity) 216 (9, $M^+$), 200 (28), 120 (100). Exact mass calcd for $C_7H_4O_3^{80}Se$: 215.9326. Found: 215.9309.

Example 2

Synthesis of a Selenenyl Sulfide

Selenenyl sulfide 31. Cyclic seleninate ester 19 (115 mg, 0.572 mmol) was dissolved in 40 mL of dichloromethane and cooled in an ice-bath. Benzyl thiol (202 µL, 1.72 mmol) was added and stirring was continued for 10 min. The solution turned dark violet and then yellow. The solvent was evaporated and the crude product was chromatographed (elution with 15% ethyl acetate-hexanes) to afford 153 mg (86%) of 31 as a pale yellow oil, which was stored in the refrigerator; IR (neat) 3356, 1258, 1198, 1023, 755, 695 cm$^{-1}$; $^1$H NMR (300 MHz) δ 7.75 (d, J=6.7 Hz, 1H), 7.37-7.12 (m, 8H), 4.77 (s, 2H), 4.04 (s, 2H), 1.96 (s, 1H); $^{13}$C NMR (75 MHz) δ 140.9, 137.8, 132.2, 131.8, 129.3, 128.7, 128.6, 128.5, 128.0, 127.6, 65.5, 42.3; $^{77}$Se NMR (76 MHz) δ 440.2; mass spectrum, m/z (relative intensity) 310 (8, M$^+$), 186 (18), 91 (100). Exact mass calcd for C$_{14}$H$_{14}$OS$^{80}$Se: 309.9931. Found: 309.9954. Analysis calcd for C$_{14}$H$_{14}$OSSe: C, 54.37; H, 4.56. Found: C, 54.58; H, 4.81.

Selenenyl sulfide 32. Cyclic seleninate ester 22 (22 mg, 0.10 mmol) was dissolved in 10 mL of methanol. Benzyl thiol (32 µL, 0.27 mmol) was added and the mixture was stirred for 1 h at room temperature. The product was concentrated in vacuo and recrystallised from ethyl acetate-hexanes to afford 23 mg (73%) of 32 as a white solid, mp 153-155° C.; IR (KBr) 3300-2300, 1660, 1266, 1027, 736 cm$^{-1}$; $^1$H NMR (300 MHz) δ 8.19-8.10 (m, 2H), 7.52-7.46 (m, 1H), 7.47-7.18 (m, 6H), 4.04 (s, 2H); $^{13}$C NMR (75 MHz) δ 172.2, 139.0, 138.2, 134.0, 132.6, 129.1, 128.7, 127.6, 126.3, 125.9, 42.3; $^{77}$Se NMR (57 MHz) δ 566.8; mass spectrum, m/z (relative intensity) 324 (2, M$^+$), 200 (7), 91 (100). Analysis calcd for C$_{14}$H$_{14}$O$_2$SSe: C, 52.02; H, 3.74. Found: C, 51.86; H, 3.74.

Example 3

Figure 2:
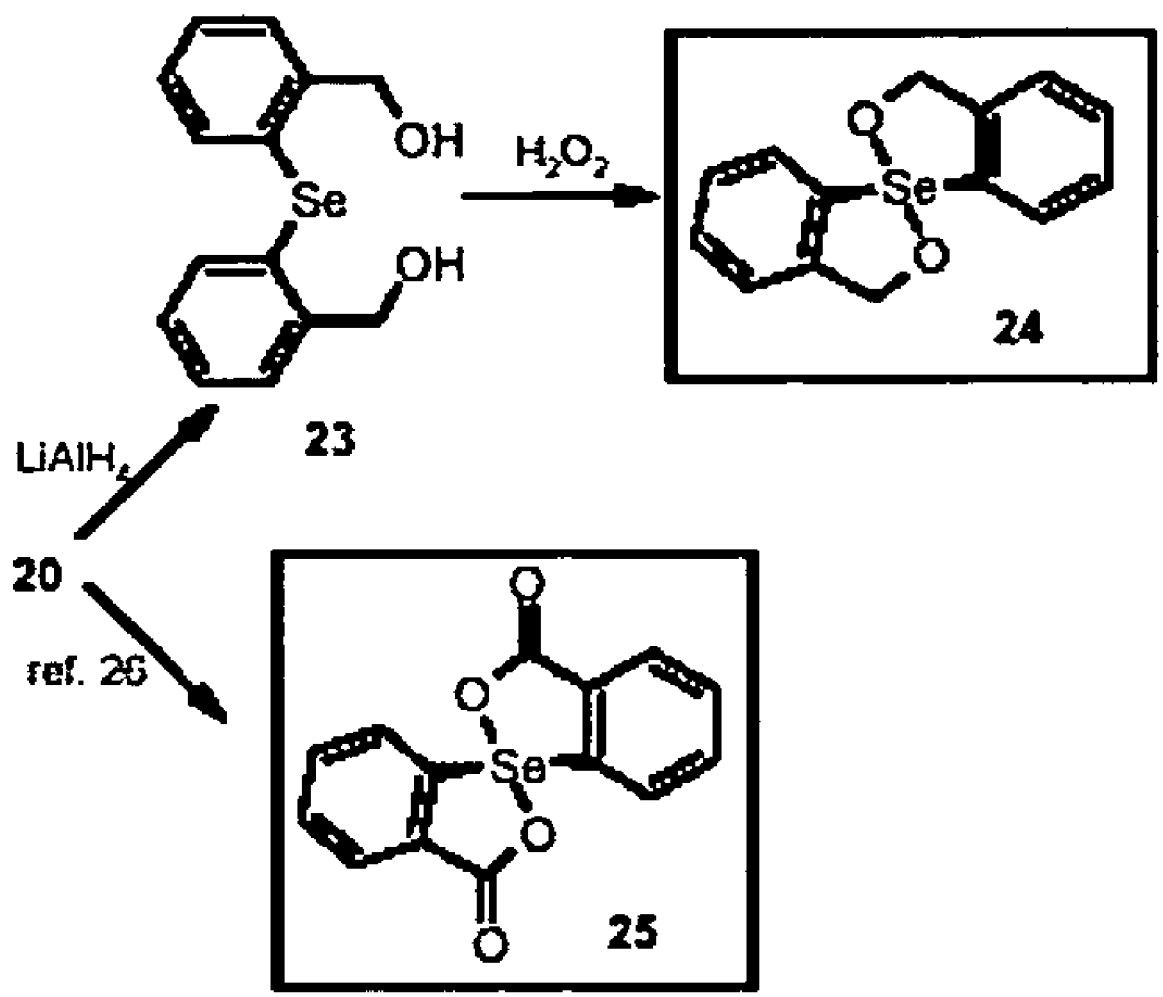
FIG. 2 is a synthetic scheme for the preparation of compounds 24 and 25.

Synthesis of a Spirodioxyselenurane (FIG. 2)

Di-2-(hydroxymethyl)phenyl selenide (23). Selenide 20 (prepared according to Dahlen, B.; Lindgren, B. Acta Chem Scand. 1973, 27, 2218; ref. 26 in FIG. 1) (360 mg, 1.12 mmol) in 15 mL of dry THF was added dropwise to a refluxing solution of 128 mg (3.36 mmol) of lithium aluminium hydride in 20 mL of dry THF under an argon atmosphere. The resulting white slurry was refluxed for an additional 90 min, cooled to room temperature and quenched cautiously with 50 mL of cold water. The mixture was filtered, the residue was washed thoroughly with ether and the filtrate was extracted repeatedly with ether. The combined organic layers were washed with saturated NaCl and water, dried and concentrated in vacuo. The product was chromatographed (elution with dichloromethane-ethyl acetate 3:1) to give 174 mg (53%) of 23 as a clear oil, which solidified upon longer standing: mp 84-86° C. (from dichloromethane-hexanes); IR (neat) 3300 (br), 1006, 733 cm$^{-1}$; $^1$H NMR (300 MHz) δ 7.47 (dd, J=6.9, 1.5 Hz, 1H), 7.35-7.27 m, 2H), 7.21-7.15 (m, 1H), 4.77 (s, 2H), 1.89 (br s, 1H); $^{13}$C NMR (75 MHz) δ 142.2, 134.6, 130.6, 129.0, 128.9, 128.5, 65.5; $^{77}$Se NMR (76 MHz) δ 316.5; mass spectrum, m/z (relative intensity) 294 (40, M$^+$), 292 (20), 246 (20), 228 (14), 195 (72), 91 (79), 77 (100). Exact mass calcd for C$_{14}$H$_{14}$O$_2$$^{80}$Se: 294.0159. Found: 294.0139.

Spirodioxyselenurane (24). Selenide 23 (114 mg, 0.389 mmol) was dissolved in 15 mL of dichloromethane and 80 µL (0.7 mmol) of 29% aqueous hydrogen peroxide was added. The mixture was stirred for 8 h at room temperature, the solvent was evaporated and the crude product was chromatographed (elution with 75% ethyl acetate-hexanes) to afford 80 mg (71%) of 24 as a white solid: mp 171-173° C. (from ethyl acetate); IR (KBr) 2798, 1441, 1201, 1008 cm$^{-1}$; $^1$H NMR (300 MHz) δ 8.03 (d, J=7.2 Hz, 1H), 7.41-7.34 (m, 2H), 7.26-7.23 (m, 1H), 5.32 (s, 2H); $^{13}$C NMR (75 MHz) δ 143.8, 134.1, 131.1, 128.2, 127.9, 124.3, 71.0; $^{77}$Se NMR (76 MHz) δ 804.4; mass spectrum, m/z (relative intensity) 292 (20, M$^+$), 291 (47), 263 (68), 77 (100). Analysis calcd for C$_{14}$H$_{12}$O$_2$Se: C, 57.74; H, 4.15. Found: C, 57.57; H, 4.18.

Spirodioxyselenurane (25). The product was obtained in 73% yield by oxidation of selenide 20 with hydrogen peroxide as described in the literature;[26] mp 326-328° C. (from ethyl acetate); lit[26] mp 310-322° C.; IR (KBr) 1695, 1269, 1104, 831, 743 cm$^{-1}$, $^1$H NMR (300 MHz,) δ 8.25-8.10 (m, 4H), 7.90-7.75 (m, 4H); $^{13}$C NMR (75 MHz, DMSO-d$_6$) δ 169.8, 142.7, 136.2, 133.9, 130.4, 130.2, 127.1. Analysis calcd for C$_{14}$H$_8$O$_4$Se: C, 52.68; H, 2.53. Found: C, 52.25; H 2.43.

Example 4

Figure 3:
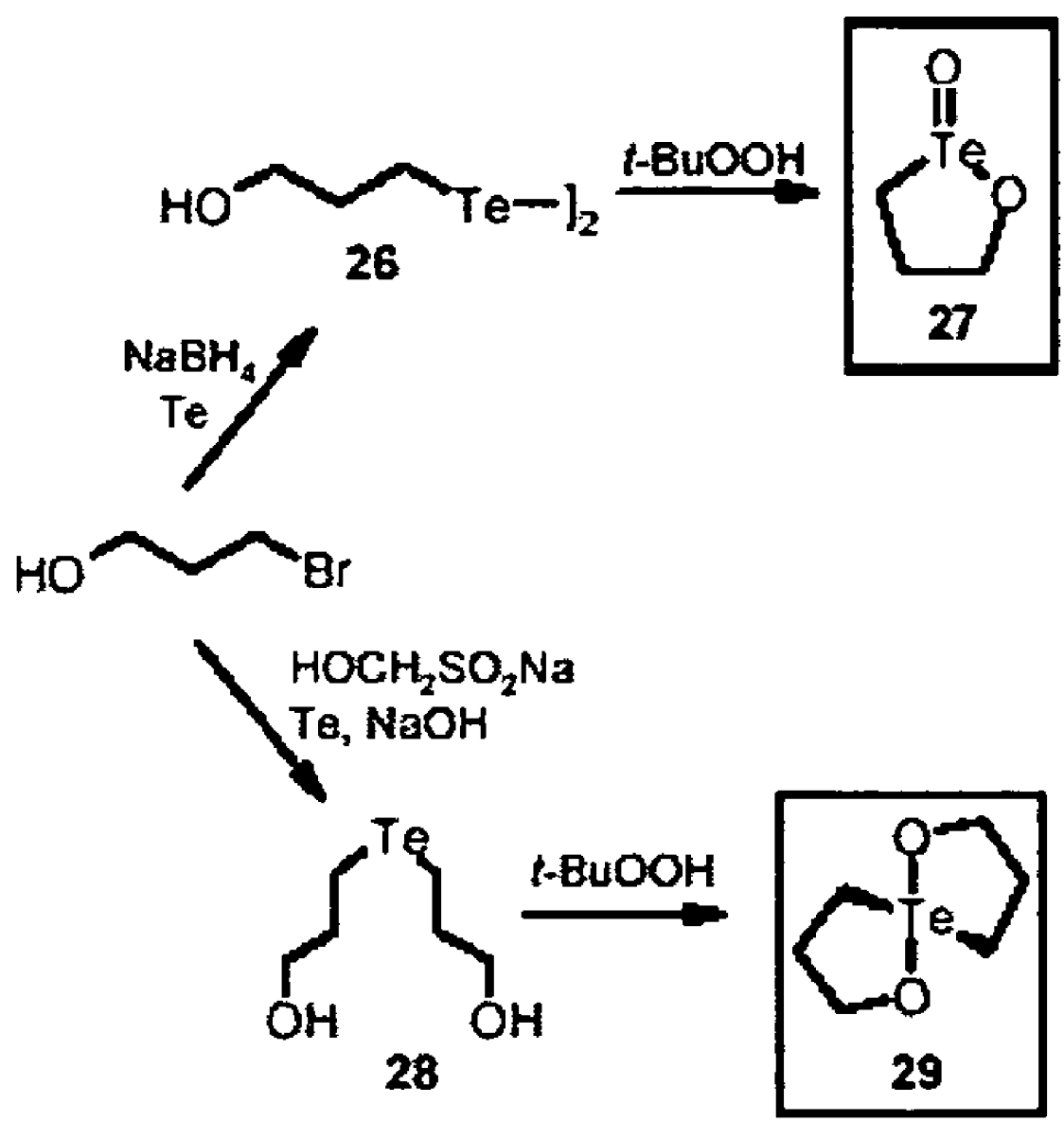
FIG. 3 is a synthetic scheme for the preparation of compounds 27 and 29.

Synthesis of an Oxatellurolane Te-Oxide (FIG. 3)

Di(3-hydroxypropyl) Ditelluride (26). Water (30 mL) was added dropwise to 2.08 g (16.3 mmol) of tellurium powder and 0.62 g (16 mmol) of sodium borohydride under argon. The mixture was heated until the tellurium dissolved to afford a dark red solution. After it was cooled to room temperature, 2.27 g (16.3 mmol) of 3-bromo-1-propanol and 5 mL of water were added. The solution turned orange and was stirred for an additional 3 h. The mixture was extracted with ether, the combined organic phases were dried, concentrated in vacuo and chromatographed (elution with 60% ethyl acetate-hexanes) to give 1.14 g (37%) of 26 as a viscous red oil: IR (neat) 3230, 1201 cm$^{-1}$; $^1$H NMR (300 MHz) δ 3.71 (t, J=6.1 Hz, 4H), 3.20 (t, J=7.2 Hz, 4H), 2.08-1.98 (m, 4H), 1.86 (br s, 2H); $^{13}$C NMR (75 MHz) δ 63.6, 36.1, −0.2; $^{125}$Te NMR (95 MHz) δ 120.0; mass spectrum, m/z (relative intensity) 378 (1, M$^+$), 256 (10), 171 (14), 130 (49), 39 (100). The deposition of tellurium from the product was observed within a few days even when the product was stored in a refrigerator. It was used without further purification.

1,2-Oxatellurolane Te-oxide (27). tert-Butyl hydroperoxide (750 µL of 56% solution, 4.5 mmol) was added to ditelluride 26 (241 mg, 0.646 mmol) in 35 mL of dichloromethane. The color of the ditelluride was discharged within 5 min. After an additional 30 min, the solution was concentrated in vacuo and the product was precipitated from methanol to afford 151 mg (58%) of 27 as a white solid: mp 257-260° C.; IR (KBr) 1033, 979, 664 cm$^{-1}$; $^1$H NMR (300 MHz, D$_2$O) δ 4.23 (t, J=5.3 Hz, 2H), 3.11 (t, J=6.7 Hz, 2H), 2.21-2.16 (m, 2H); $^{13}$C NMR (100 MHz, D$_2$O) δ 70.2, 46.9, 27.6; $^{125}$Te NMR (95 MHz, D$_2$O) δ 1042.0; mass spectrum, m/z (relative intensity); mass spectrum, m/z (relative intensity) 204 (5, M$^+$), 188 (66), 130 (100). Exact mass calcd for C$_3$H$_6$O$_2$$^{130}$Te: 203.9430. Found: 203.9418. Analysis calcd for C$_3$H$_6$O$_2$Te: C, 17.87; H, 3.00. Found: C, 18.19; H, 2.95.

Example 5

Synthesis of a Spirodioxytellurane (FIG. 3)

Di(3-hydroxypropyl) telluride (28). Hydroxymethanesulfinic acid monosodium salt dihydrate (3.0 g, 19 mmol) was added to 0.50 g (3.9 mmol) of tellurium powder and 2.5 g (63 mmol) of sodium hydroxide in 30 mL of water. The dark red mixture was refluxed under argon until it formed a pale pink solution (ca. 30 min). The solution was cooled to room temperature and 0.69 mL (7.6 mmol) of 3-bromo-1-propanol was added. The mixture turned yellow within 5 min and was stirred for an additional 30 min. The product was extracted with ether, dried, concentrated in vacuo and chromatographed (elution with ethyl acetate) to give 0.51 g (55%) of 28 as a yellow oil: IR (neat) 3340, 1221 cm$^{-1}$, $^1$H NMR (300 MHz) δ 3.72 (t, J=6.0 Hz, 4H), 2.74 (t, J=7.4 Hz, 4H), 2.07-1.98 (m, 4H), 1.80 (br s, 2H); $^{13}$C NMR (75 MHz) δ 64.0, 34.7, −1.4; $^{125}$Te NMR (95 MHz) δ 229.5; mass spectrum, m/z (relative intensity) 248 (53, M$^+$), 189 (20), 172 (53), 130 (26), 57 (56), 41 (100). Exact mass calcd for $C_6H_{14}O_2{}^{130}Te$: 248.0056. Found: 248.0044 The air-sensitive product was used directly without further purification.

Spirodioxytellurane (29). tert-Butyl hydroperoxide (550 μL of 38% solution, 2.2 mmol) was added to 524 mg (2.13 mmol) of telluride 28 in 15 mL of dichloromethane. The yellow mixture turned colorless and clear within 5 min and was stirred at room temperature for an additional 30 min. The solvent was evaporated under vacuum to give a colorless oil, which solidified upon standing to give 489 mg (94%) of 29 as a colorless oil, which solidified to a waxy solid on standing; IR (neat) 1137, 1040, 982 cm$^{-1}$; $^1$H NMR (300 MHz) δ 4.25-4.18 (m, 2H), 3.79-3.72 (m, 2H), 2.90-2.73 (m, 4H), 2.30-2.12 (m, 2H), 1.95-1.73 (m, 2H); $^{13}$C NMR (75 MHz) δ 67.4, 28.5, 27.2; $^{125}$Te NMR (126 MHz) δ 1095.8; mass spectrum, m/z (relative intensity) 246 (1, M$^+$), 188 (42), 130 (39), 43 (56). Exact mass calcd for $C_6H_{12}O_2{}^{130}Te$: 245.9900. Found: 245.9911. Analysis calcd for $C_6H_{12}O_2Te$: C, 29.56; H. 4.96. Found: C, 29.42; H, 5.05.

Example 6

Preparation of Additional Compounds

Preparation of 2,2'-diselenobis(5-methoxybenzyl alcohol) (100)

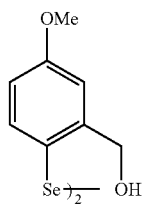

In a flame-dried 100 mL round bottom flask, 300 mg (1.38 mmol) of 2-bromo-5-methoxybenzyl alcohol were dissolved in 15 mL of dry tetrahydrofuran, cooled to −78° C. under a nitrogen atmosphere and treated with tert-butyllithium (2.5 mL, 4.2 mmol). After stirring for 40 minutes, selenium powder (330 mg, 4.2 mmol) was added and the cooling bath was removed. The mixture was stirred for 5 hours under a nitrogen atmosphere at room temperature to dissolve the selenium, forming a red solution. Additionally, the flask was opened and the mixture was stirred overnight in the presence of air, followed by quenching with 1 M hydrochloric acid (8 mL), extraction with diethyl ether, washing with sat. ammonium chloride, drying and concentration in vacuo. The final product was chromatographed (50% hexane-ethyl acetate) to give 173 mg (58%) of yellow oil, which solidified upon standing, m.p. 103-104° C. (from ethanol/hexane) IR (KBr) 3337 (broad), 2934, 2832, 1585, 1566, 1465, 1294, 1222, 1163, 1056, 1014, 815, 795 cm$^{-1}$; $^1$H NMR (300 MHz) δ 7.47 (d, J=8.7 Hz, 1H), 7.04 (d, J=3.1 Hz, 1H), 6.74 (dd, J=8.7 Hz, 3.1 Hz, 1H), 4.65 (s, 2 H), 3.84 (s, 3H), 2.05 (brs, 1H); $^{13}$C NMR (75 MHz) δ 161.3, 145.7, 139.1, 120.5, 114.2, 114.0, 65.6, 55.5; $^{77}$Se NMR (76 MHz) δ 452.6; mass spectrum, m/z (relative intensity) 432 (8, M$^+$), 405 (16), 256 (18), 200 (58), 108 (100), 71 (55), 57 (93), 43 (69). Exact mass calcd for $C_{16}H_{18}O_4{}^{80}Se^{78}Se$: 431.9543. Found: 431.9557.

Preparation of allyl (2-hydroxymethyl-4-methoxy)phenyl selenide (101)

Diselenide 100 (173 mg, 0.4 mmol) was dissolved in 10 mL of dry tetrahydrofuran, cooled to 0° C. and treated with sodium borohydride (68 mg, 1.80 mmol). Additionally, 2 mL of absolute ethanol were added dropwise to aid dissolution of sodium borohydride. After vigorous reaction and evolution of hydrogen subsided, the solution was stirred under nitrogen until it turned pale yellow (ca. 5 min), indicating the formation of the selenolate ion. Following the addition of allyl iodide (73 μL, 0.8 mmol), the mixture was stirred at room temperature for 2.5 hours. Then, 1 M hydrochloric acid (5 mL) was added and mixture was extracted with diethyl ether, dried, concentrated and chromatographed (elution with 40% ethyl acetate-hexanes) to give 137 mg (67%) of clear oil. IR (neat) 3371 (broad), 2934, 1591, 1470, 1293, 1234, 1053, 1018, 914, 813 cm$^{-1}$; $^1$H NMR (300 MHz) δ 7.49 (d, J=8.7 Hz, 1H), 7.00 (d, J=2.6 Hz, 1 H), 6.75 (dd, J=7.2 Hz, 3.1 Hz, 1H), 5.94-5.86 (m, 1H), 4.90 (dd, J=10.3 Hz, 1.6 Hz, 1H), 4.81 (dd, J=15.4 Hz, 1.6 Hz, 1H), 4.76 (d, J=6.2 Hz, 2H), 3.81 (s, 3H), 3.40 (d, J=7.2 Hz, 2H), 2.48 (t, J=6.2 Hz, 1H); $^{13}$C NMR (75 MHz) δ 160.2, 145.6, 138.3, 134.5, 118.9, 116.9, 114.0, 65.8, 55.4, 31.1; mass spectrum, m/z (relative intensity) 258 (16, M$^+$), 217 (12, M$^+$-C$_3$H$_5$), 136 (17), 108 (100), 39 (21). Exact mass calcd for $C_{11}H_{14}O_2{}^{80}Se$: 258.0159. Found: 258.0140

Preparation of 5-metboxybenzo-1,2-oxaselenolane Se-oxide (91)

Cyclic seleninate 91 was prepared in 81% yield by oxidation of allyl selenide 101 with 5 equivalents of 58% hydrogen peroxide to afford the product as a fine white powder after recrystallization from ethyl acetate, with mp 169-170° C. IR (KBr) 3002, 1600, 1470, 1280, 1239, 1152, 1049, 983, 830, 555 cm$^{-1}$; $^1$H NMR (300 MHz) δ 7.67 (d, J=8.7 Hz, 1H), 7.04 (dd, J=8.7 Hz, 2.0 Hz, 1H), 6.94 (d, J=2.0 Hz, 1H), 5.93 (d, J=13.8 Hz, 1H), 5.55 (d, J=13.8 Hz, 1H), 3.88 (s, 3H); $^{13}$C NMR (75 MHz) δ 163.0, 146.6, 139.8, 126.6, 115.9, 107.3, 78.2, 55.9; $^{77}$Se NMR (57 MHz) δ 1348.8; mass spectrum, m/z (relative intensity) 232 (5, M$^+$), 216 (11, M$^+$-O), 136 (84, M$^+$-SeO), 108 (41), 43 (100). Exact mass calcd for $C_8H_8O_3{}^{80}Se$: 231.9639. Found: 231.99646. Analysis calcd for $C_7H_6O_2Se$: C, 41.58; H, 3.49. Found: C, 41.61; H 3.60.

Preparation of 2,2'-diselenobis(5fluorobenzoic acid) (116)

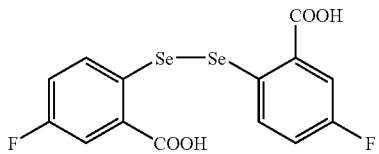

To a stirred solution containing 5.0 g (32 mmol) of 2-amino-5-fluorobenzoic acid and 4.8 mL of concentrated hydrochloric acid in 50 mL of water cooled in an ice bath to 0° C., were added dropwise 2.36 g (34 mmol) of sodium nitrite in 30 mL of water while maintaining the temperature below 5° C. The resulting solution of the corresponding diazonium salt was stirred for 20 min while a solution of potassium diselenide was prepared in the following fashion. Selenium (5.1 g, 65 mmol) and potassium hydroxide (16 g, 40 mmol) were melted in a 500 mL round bottom flask. Cold water (80 mL) was added to produce a red aqueous solution of potassium diselenide, which was subsequently cooled to 0° C. The pH of the diazonium salt was adjusted to 6 with solid sodium acetate and this mixture was added dropwise to the potassium diselenide solution. The resulting mixture was stirred for 0.5 hours at room temperature, then slowly warmed to 80° C., cooled to room temperature and filtered to remove red selenium. The filtrate was acidified with concentrated hydrochloric acid yielding 5.95 g (85%) of an orange solid with m.p. 263-266° C. This compound was used without any further purification. IR (KBr) 3421-2550 (broad), 1675, 1460, 1423, 1257, 1202, 824, 762; $^1$H NMR (300 MHz, Acetone-d$_6$) δ 7.87 (dd, J=9.2 Hz, 3.1 Hz, 1H), 7.79 (dd, J=8.7 Hz, 5.1 Hz, 1H), 6.74 (dt, J=8.2 Hz, 3.1 Hz, 1 H; mass spectrum, m/z (relative intensity) 438 (8, M$^+$), 358 (21), 219 (54), 202 (100), 174 (94), 131 (49), 71 (10). Exact mass calcd for $C_{14}H_8O_4F_2{}^{80}Se_2$: 437.8721. Found: 437.8736.

Preparation of allyl (4-fluoro-2-hydroxymethyl)phenyl selenide (117)

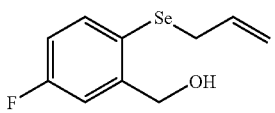

Compound 117 was prepared in 72% yield by the reduction of diacid 116 with lithium aluminum hydride followed by alkylation with allyl iodide. The product was chromatographed (elution with 40% ethyl acetate-hexanes) and had: IR (neat, NaCl) 3304 (broad), 3073, 2926, 1626, 1600, 1579, 1464, 1268, 1226, 1146, 1104, 1028, 986, 917, 873, 813 cm$^{-1}$; $^1$H NMR (300 MHz) δ 7.55-7.49 (dd, J=8.4 Hz, 5.8 Hz, 1H), 7.20 (dd, J=9.5 Hz, 2.7 Hz, 1H), 6.95-6.84 (dt, J=8.3 Hz, 2.8 Hz, 1H), 5.96-5.82 (m, 1H), 4.91 (d, J=9.9 Hz, 1H), 4.83 (d, J=17.1 Hz, 1H), 4.76 (d, J=5.8 Hz, 2H), 3.44 (d, J=7.6 Hz, 2H), 2.39 (t, J=5.9 Hz, 1H); mass spectrum, m/z (relative intensity) 246 (24, M$^+$), 205 (31, M$^+$-C$_3$H$_5$), 177 (9), 147 (14), 123 (10), 96 (100), 75 (10), 41 (37). Exact mass calcd for $C_{10}H_{11}OF^{80}Se$: 245.9959. Found: 245.9941. Analysis calcd for C$_{10}$H$_{11}$FOSe: C, 48.99; H, 4.52. Found: C, 48.89; H, 4.77.

Preparation of 5-fluorobenzo-1,2-oxaselenolane Se-oxide (93)

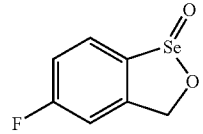

Compound 93 was prepared by the oxidation of allyl selenide 117 with 65% tert-butyl hydroperoxide in dichloromethane and after concentration, was recrystallized from ethyl acetate in 78% yield. The product was a white fine powder with mp 141-142° C.; IR (KBr) 3073, 2947, 1579, 1460, 1450, 1424, 1250, 1231, 1134, 989, 927, 861, 830, 795, 562, 449 cm$^{-1}$; $^1$H NMR (300 MHz) δ 7.93-7.89 (dd, J=9.2 Hz, 5.0 Hz, 1H), 7.27-7.09 (m, 2H), 5.88 (d, J=1H), 5.53 (d, J=14.1 Hz, 1H); mass spectrum, m/z (relative intensity) 220 (12, M$^+$), 201 (3, M$^+$-F), 124 (51), 96 (100), 50 (21). Exact mass calcd for $C_7H_5O_2F^{80}Se$: 219.9439. Found: 219.9455. Analysis calcd for C$_7$H$_5$O$_2$FSe: C, 38.38; H, 2.30. Found: C, 37.57; H, 2.58.

Preparation of 2,2'-selenobis(5-methoxybenzyl alcohol) (133)

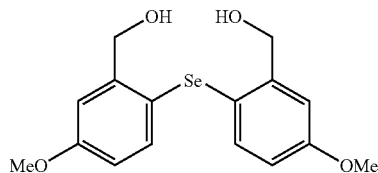

In a flame-dried 50 mL round bottom flask, 700 mg (3.22 mmol) of 2-bromo-5-methoxybenzyl alcohol were dissolved in 10 mL of dry tetrahydrofuran, cooled to −78° C. under nitrogen and slowly treated with tert-butyllithium (4.0 mL, 6.8 mmol). After stirring the mixture at −78° C. for 40 minutes, it was slowly treated with selenium (II) diethylthiocarbamate (Se(dtc)$_2$ (1.36 g, 3.64 mmol) dissolved in 15 mL of dry tetrahydrofuran. After the cooling bath was removed, the mixture was stirred at room temperature for 6 hours and quenched with 1 M hydrochloric acid (15 mL). After washing with brine, extracting with ethyl acetate, drying and concentrating, the final product was chromatographed (elution with 50% hexane-ethyl acetate) to give 208 mg (37%) of a clear solid with mp 77-78° C. IR (neat) 3355 (broad), 2935, 1591, 1472, 1234, 1051, 1016, 859, 734 cm$^{-1}$; $^1$H NMR (300 MHz) δ 7.27 (d, J=10.8 Hz, 1H), 7.02 (d, J=2.6 Hz, 1H), 6.70 (dd, J=8.7 Hz, 3.1 Hz, 1H), 4.66 (s, 2H), 3.79 (s, 3H), 2.52 (br s, 1H); $^{13}$C NMR (75 MHz) δ 159.9, 143.8, 135.9, 120.6, 114.4, 114.3, 65.3, 55.5; mass spectrum, m/z (relative intensity) 354 (61, M$^+$), 256 (47), 214 (37), 200 (25), 135 (44), 121 (87), 108 (100), 77 (47). Exact mass calcd for $C_{16}H_{16}O_4{}^{80}Se$: 354.0370. Found: 354.0366.

Preparation of spirodioxyselenurane 126

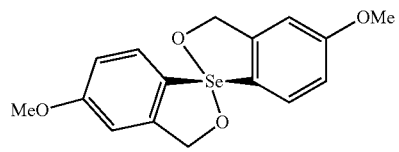

Compound 126 was prepared in 98% yield by oxidation of selenide 133 with 65% tert-butyl hydroperoxide in dichloromethane. It was recrystallized from ethyl acetate-hexanes (1:1) as white powder with mp 171-173° C. IR (KBr) 2916, 1581, 1469, 1276, 1234, 1027, 902, 872, 796 cm$^{-1}$; $^1$H NMR (300 MHz) δ 7.89 (d, J=8.7 Hz, 1H), 6.92 (dd, J=8.2 Hz, 2.0 Hz, 1H), 6.76 (d, J=2.0 Hz, 1H), 5.29 (d, J=3.1 Hz, 2H), 3.81 (s, 3H); $^{13}$C NMR (75 MHz) δ 163.9, 147.5, 130.4, 127.0, 115.9, 110.3, 72.4, 57.2; $^{77}$Se NMR (57 MHz) δ 801.0; mass spectrum, m/z (relative intensity) 352 (37, M$^+$), 321 (11, M$^+$-OCH$_3$), 305 (27), 214 (40), 135 (44), 108 (70), 77 (62), 63 (100). Exact mass calcd for $C_{16}H_{16}O_4Se$: 352.0214. Found: 352.0206. Analysis calcd for $C_{16}H_{16}O_4Se$: C, 54.71; H, 4.59. Found: C, 53.89; H, 4.48.

Preparation of 2,2'-diselenobis(5-fluorobenzyl alcohol) (137)

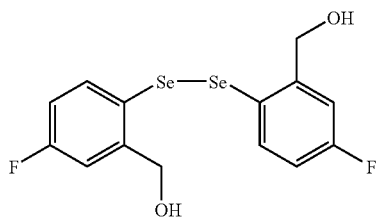

To lithium aluminum hydride (0.89 g, 23 mmol) in dry tetrahydrofuran (20 mL) under argon at room temperature, 2,2'-diselenobis(5-fluorobenzoic acid) (116) (2.05 g, 4.70 mmol) dissolved in 10 mL of dry tetrahydrofuran was added dropwise. After refluxing for 50 minutes, the mixture was quenched with 20 mL of water and extracted with ethyl acetate. The aqueous solution was left sitting overnight with consequent precipitation of 815 mg (42%) of 137 as yellow needles with mp 112° C. IR (KBr) 3214 (broad), 1577, 1016, 874, 814 cm$^{-1}$; $^1$H NMR (300 MHz) δ 7.52 (dd, J=8.2 Hz, 5.6 Hz, 1H), 7.24 (dd, J=9.8 Hz, 1H), 6.89 (dt, J=8.2 Hz, 3.1 Hz, 1 H), 4.69 (s, 2H), 2.06 (br s, 1H); mass spectrum, m/z (relative intensity) 410 (10, M$^+$), 188 (23), 123 (16), 96 (100), 75 (16). Exact mass calcd for C14H12O$_2$F$_2$$^{80}$Se: 409.9134. Found: 409.9132.

Preparation of 2,2'-selenobis(5-fluorobenzyl alcohol) (135)

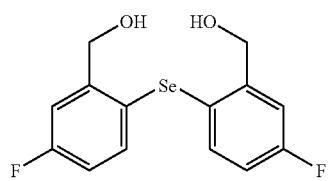

2-Amino-5-fluorobenzyl alcohol (90 mg, 0.64 mmol) suspended in 2 mL of water was cooled to 0° C. and treated with 0.33 mL of concentrated hydrochloric acid followed by dropwise addition of sodium nitrite (53 mg, 0.77 mmol) in one mL of water. The diazonium salt was stirred at 0° C. for 10 minutes. Meanwhile, diselenide 136 (104 mg, 0.25 mmol) was dissolved in 8 mL of tetrahydrofuran-water (1:1) mixture, cooled to 0° C. under argon and treated with sodium borohydride (29 mg, 0.77 mmol). After the vigorous reaction subsided with formation of a clear solution of the corresponding selenolate anion, this mixture was treated dropwise with the diazonium salt, the pH of which was adjusted prior to use to 5.5 with saturated solution of sodium acetate. The addition of the diazonium salt was accompanied by a vigorous reaction. The reaction mixture was then warmed to room temperature and stirred for 1 hour followed by the addition of ethyl acetate (10 mL) and saturated ammonium chloride (5 mL). The organic phase was separated, dried and concentrated to give a red-brown oil, which was chromatographed (elution with 40% ethyl acetate-hexanes). The final product 135 (56.7 mg, 34%) was obtained as a pale yellow oil, which solidified upon standing; m.p. 109-111° C. IR (neat, NaCl) 3291 (broad), 1464, 1268, 1025, 813 cm$^{-1}$; $^1$H NMR (300 MHz) δ 7.27-7.19 (m, 2H), 6.91-6.84 (dt, J=8.3 Hz, 2.9 Hz, 1H), 4.68 (s, 2H), 2.57 (br s, 1H); mass spectrum, m/z (relative intensity) 330 (65, M$^+$), 281 (15, M$^+$–CH$_2$OF), 232 (58, M$^+$-C$_2$H$_4$O$_2$F$_2$), 214 (29), 202 (45), 123 (39), 109 (73), 96 (100). Exact mass calcd for $C_{14}H_{12}O_2F_2^{80}Se$: 329.9971. Found: 329.9946. Analysis calcd for $C_{14}H_{12}O_2F_2Se$: C, 51.08; H, 3.67 Found: C, 50.45; H, 3.80.

Preparation of spirodioxyselenurane 127

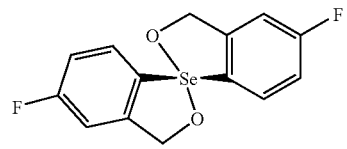

Compound 127 was prepared by oxidation of selenide 135 with 65% tert-butyl hydroperoxide in dichloromethane. It was recrystallized from ethyl acetate to afford 97% of a white powder with mp 189-191° C. IR (KBr) 3095, 2817, 1581, 1456, 1419, 1250, 1026, 928, 860, 821, 759 cm$^{-1}$; $^1$H NMR (400 MHz) δ 7.97 (dd, J=8.8 Hz, 5.0 Hz, 1H), 7.08 (dt, J=8.6 Hz, 2.5 Hz, 1H), 6.96 (dd, J=8.3 Hz, 2.5 Hz, 1H), 5.32 (d, J=14.9 Hz, 1H), 5.26 (d, J=14.9 Hz, 1H); mass spectrum, m/z (relative intensity) 328 (3, M$^+$), 297 (25), 256 (11), 173 (9), 71 (44), 43 (100); Exact mass calcd for $C_{14}H_9O_2F_2^{80}Se$: 326.9736. Found: 326.9750.

Example 7

Figure 4:
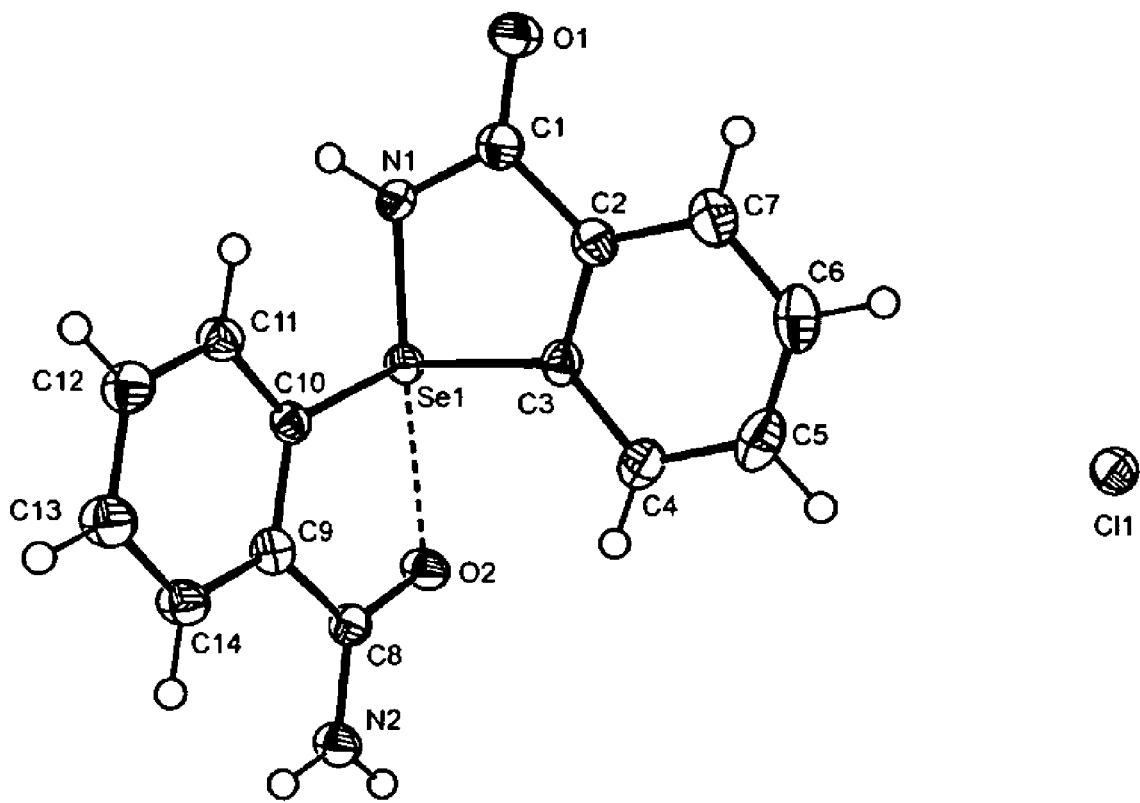
FIG. 4 is an X-ray crystal structure of compound 12.

Synthesis and X-Ray Data of Compound 12 (FIG. 4)

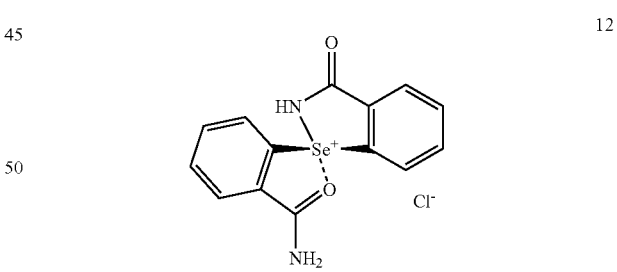

2,2'-Selenobisbenzamide (178 mg, 0.56 mmol) was dissolved in 30 mL of methanol-dichloromethane (1:1) solution and cooled in an ice-bath to 5° C. This was treated with 150 mg (1.12 mmol) of N-chlorosuccinimide dissolved in 5mL of methanol/dichloromethane (1:1). The mixture was stirred at room temperature for 5 hours, concentrated and washed with ethyl acetate to give a crude product, which was recrystallized from glacial acetic acid to give 160 mg (81%) of 12 as a white solid with mp 286-287° C. IR (KBr) 3268, 3094, 1665, 1595, 1550, 1456, 1432, 1298, 743 cm$^{-1}$; $^1$H NMR (300 MHz, DMSO-d6) δ 10.67 (br s, 1H), 9.77 (br s, 1H), 9.33 (br s, 1H), 8.42 (d, J=6.9 Hz, 1H), 8.43-7.78 (m, 7H); $^{13}$C NMR (75

MHz, DMSO-$d_6$) δ 171.1, 170.0, 140.5, 140.0, 136.0, 135.9, 133.8, 133.4, 130.4, 130.1, 129.8, 129.2, 127.8, 126.2; $^{77}$Se NMR (57 MHz, DMSO-$d_6$) δ 1658.5; mass spectrum (ESI) 319 (M−Cl+H)$^+$, 341 (M−Cl+Na)$^+$.

A colorless prismatic crystal of $C_{14}H_{13}ClN_2O_3Se$ (includes a coordinating water molecule not shown in the ORTEP diagram) was coated with Paratone 8277 oil (Exxon) and mounted on a glass fiber. All measurements were made on a Nonius KappaCCD diffractometer with graphite monochromated Mo—Kα radiation. Cell constants obtained from the refinement (Otwinowski, Z. & Minor, W. (1997). "Processing of X-ray Diffraction Data Collected in Oscillation Mode", Methods in Enzymology, Volume 276: Macromolecular Crystallograpy, part A, p. 307-326, C. W. Carter, Jr. & R. M. Sweet, Eds., Academic Press.) of 6428 reflections in the range 3.8<θ<27.4° corresponded to a primitive triclinic cell; details of crystal data and structure refinement have been provided in Table 1. The data were collected (Hooft, R. (1998). COLLECT: Users Manual, Nonius B. V., Delft. The Netherlands.) at a temperature of 173(2) K. using the ω and φ scans to a maximum θ value of 27.4°. The data were corrected for Lorentz and polarization effects and for absorption using multi-scan method (Otwinowski, Z. & Minor, W. (1997), op. cit.). Since the crystal did not show any sign of decay during data collection a decay correction was deemed unnecessary.

The structure was solved by the direct methods (Altomare, A., Cascarano, M., Giacovazzo, C. & Guagliardi, A. (1993). Completion and Refinement of Crystal Structures with SIR92. J. Appl. Cryst., 26, 343-350.) and expanded using Fourier techniques (Beurskens, P. T., Admiraal, G., Beurskens, G., Bosman, W. P., de Gelder, R., Israel, R. & Smits, J. M. M. (1994). The DIRDIF-94 program system, Technical Report of the Crystallography Laboratory, University of Nijmegen, The Netherlands.). The non-hydrogen atoms were refined anisotropically. A disordered water molecule was also located in the structure. Hydrogen atoms were located from a difference map, were included at geometrically idealized positions and were not refined; H-atoms of the disordered water of solvation were ignored. The final cycle of full-matrix least-squares refinement using SHELXL97 (Sheldrick, G. M. (1997). SHELXL97—A Program for Refinement of Crystal Structures, University of Göttingen, Germany.) converged with unweighted and weighted agreement factors, R=0.036 and wR=0.084 (all data), respectively, and goodness of fit, S=1.05. The weighting scheme was based on counting statistics and the final difference map was free of any chemically significant features. The figure was plotted with the aid of ORTEPII (Johnson, C. K. (1976). ORTEPII. Report ORNL-5138. Oak Ridge National Laboratory, Tennessee, USA.).

TABLE 1

Crystal data and structure refinement for $C_{14}H_{13}ClN_2O_3Se$.

| | |
|---|---|
| Empirical formula | $C_{14}H_{13}ClN_2O_3Se$ (includes 1 mole $H_2O$ |
| Formula weight | 371.67 |
| Temperature | 173(2) K |
| Wavelength | 0.71073 Å |
| Crystal system | Triclinic |
| Space group | P −1 |
| Unit cell dimensions | a = 7.9440(3) Å α = 81.649(3)°. |
| b = 9.7000(4) Å | β = 74.131(3)°. |
| c = 11.0010(3) Å | γ = 67.2410(19)°. |
| Volume | 751.16(5) Å$^3$ |
| Z | 2 |
| Density (calculated) | 1.643 Mg/m$^3$ |
| Absorption coefficient | 2.688 mm$^{-1}$ |
| F(000) | 372 |
| Crystal size | 0.06 × 0.05 × 0.04 mm$^3$ |

TABLE 1-continued

Crystal data and structure refinement for $C_{14}H_{13}ClN_2O_3Se$.

| | |
|---|---|
| Theta range for data collection | 3.8 to 27.4°. |
| Index ranges | −10 <= h <= 10, −12 <= k <= 12, −14 <= l <= 14 |
| Reflections collected | 6428 |
| Independent reflections | 3416 [R(int) = 0.032] |
| Completeness to theta = 27.4° | 99.3% |
| Absorption correction | Multi-scan method |
| Max. and min. transmission | 0.900 and 0.855 |
| Refinement method | Full-matrix least-squares on F$^2$ |
| Data/restraints/parameters | 3416/0/194 |
| Goodness-of-fit on F$^2$ | 1.05 |
| Final R indices [I > 2sigma(I)] | R1 = 0.036, wR2 = 0.079 |
| R indices (all data) | R1 = 0.051, wR2 = 0.084 |
| Largest diff. peak and hole | 0.50 and −0.54 e.Å$^{-3}$ |

TABLE 2

Atomic coordinates (×10$^4$) and equivalent isotropic displacement parameters (Å$^2$ × 10$^3$) for $C_{14}H_{13}ClN_2O_3Se$. U(eq) is defined as one third of the trace of the orthogonalized U$^{ij}$ tensor.

| Atom | x | y | z | U(eq) |
|---|---|---|---|---|
| Se(1) | 2398(1) | 3448(1) | 8510(1) | 20(1) |
| Cl(1) | 1950(1) | 4235(1) | 1330(1) | 25(1) |
| O(1) | 2295(3) | 7491(2) | 7352(2) | 33(1) |
| O(2) | 2591(3) | 1086(2) | 8179(2) | 26(1) |
| N(1) | 2603(3) | 5290(3) | 8503(2) | 23(1) |
| N(2) | 4578(3) | −1311(3) | 8212(2) | 27(1) |
| C(1) | 2457(4) | 6181(3) | 7434(3) | 24(1) |
| C(2) | 2520(4) | 5331(3) | 6394(3) | 23(1) |
| C(3) | 2551(4) | 3889(3) | 6720(2) | 22(1) |
| C(4) | 2566(4) | 2967(4) | 5852(3) | 29(1) |
| C(5) | 2540(5) | 3570(4) | 4627(3) | 38(1) |
| C(6) | 2506(5) | 5008(4) | 4288(3) | 36(1) |
| C(7) | 2512(4) | 5898(4) | 5161(3) | 32(1) |
| C(8) | 4167(4) | 136(3) | 8264(3) | 21(1) |
| C(9) | 5591(4) | 700(3) | 8423(2) | 22(1) |
| C(10) | 5015(4) | 2243(3) | 8511(2) | 20(1) |
| C(11) | 6222(4) | 2886(3) | 8656(3) | 23(1) |
| C(12) | 8047(4) | 1968(3) | 8693(3) | 28(1) |
| C(13) | 8650(4) | 436(3) | 8599(3) | 31(1) |
| C(14) | 7419(4) | −202(3) | 8466(3) | 27(1) |
| O(3A) | 2791(17) | 9546(11) | 5082(10) | 162(4) |
| O(3B) | 730(20) | 10190(18) | 5 084(15) | 162(4) |

TABLE 3

Bond lengths [Å] and angles [°] for $C_{14}H_{13}ClN_2O_3Se$.

| | |
|---|---|
| Se(1)—N(1) | 1.854(2) |
| Se(1)—C(3) | 1.934(3) |
| Se(1)—C(10) | 1.952(3) |
| Se(1)—O(2) | 2.3124(19) |
| O(1)—C(1) | 1.219(3) |
| O(2)—C(8) | 1.253(3) |
| N(1)—C(1) | 1.358(4) |
| N(1)—H(1) | 0.8800 |
| N(2)—C(8) | 1.318(4) |
| N(2)—H(2A) | 0.8800 |
| N(2)—H(2B) | 0.8800 |
| C(1)—C(2) | 1.484(4) |
| C(2)—C(3) | 1.385(4) |
| C(2)—C(7) | 1.389(4) |
| C(3)—C(4) | 1.395(4) |
| C(4)—C(5) | 1.391(4) |
| C(4)—H(4) | 0.9599 |
| C(5)—C(6) | 1.382(5) |
| C(5)—H(5) | 0.9600 |
| C(6)—C(7) | 1.383(5) |
| C(6)—H(6) | 0.9601 |
| C(7)—H(7) | 0.9600 |
| C(8)—C(9) | 1.492(4) |

TABLE 3-continued

Bond lengths [Å] and angles [°] for C₁₄H₁₃ClN₂O₃Se.

| | |
|---|---|
| C(9)—C(14) | 1.385(4) |
| C(9)—C(10) | 1.395(4) |
| C(10)—C(11) | 1.382(4) |
| C(11)—C(12) | 1.385(4) |
| C(11)—H(11) | 0.9600 |
| C(12)—C(13) | 1.384(4) |
| C(12)—H(12) | 0.9600 |
| C(13)—C(14) | 1.390(4) |
| C(13)—H(13) | 0.9602 |
| C(14)—H(14) | 0.9599 |
| O(3B)—O(3B)#1 | 1.41(3) |
| N(1)—Se(1)—C(3) | 85.02(11) |
| N(1)—Se(1)—C(10) | 96.20(11) |
| C(3)—Se(1)—C(10) | 101.39(11) |
| N(1)—Se(1)—O(2) | 169.26(9) |
| C(3)—Se(1)—O(2) | 87.29(10) |
| C(10)—Se(1)—O(2) | 77.97(9) |
| C(8)—O(2)—Se(1) | 110.23(17) |
| C(1)—N(1)—Se(1) | 117.17(18) |
| C(1)—N(1)—H(1) | 121.4 |
| Se(1)—N(1)—H(1) | 121.4 |
| C(8)—N(2)—H(2A) | 120.0 |
| C(8)—N(2)—H(2B) | 120.0 |
| H(2A)—N(2)—H(2B) | 120.0 |
| O(1)—C(1)—N(1) | 124.3(3) |
| O(1)—C(1)—C(2) | 125.4(3) |
| N(1)—C(1)—C(2) | 110.3(2) |
| C(3)—C(2)—C(7) | 119.7(3) |
| C(3)—C(2)—C(1) | 115.8(2) |
| C(7)—C(2)—C(1) | 124.4(3) |
| C(2)—C(3)—C(4) | 122.4(3) |
| C(2)—C(3)—Se(1) | 110.61(19) |
| C(4)—C(3)—Se(1) | 126.8(2) |
| C(5)—C(4)—C(3) | 116.6(3) |
| C(5)—C(4)—H(4) | 123.5 |
| C(3)—C(4)—H(4) | 119.9 |
| C(6)—C(5)—C(4) | 121.7(3) |
| C(6)—C(5)—H(5) | 118.6 |
| C(4)—C(5)—H(5) | 119.7 |
| C(5)—C(6)—C(7) | 120.8(3) |
| C(5)—C(6)—H(6) | 120.4 |
| C(7)—C(6)—H(6) | 118.7 |
| C(6)—C(7)—C(2) | 118.8(3) |
| C(6)—C(7)—H(7) | 121.4 |
| C(2)—C(7)—H(7) | 119.9 |
| O(2)—C(8)—N(2) | 122.1(3) |
| O(2)—C(8)—C(9) | 117.5(2) |
| N(2)—C(8)—C(9) | 120.5(2) |
| C(14)—C(9)—C(10) | 119.2(3) |
| C(14)—C(9)—C(8) | 124.2(3) |
| C(10)—C(9)—C(8) | 116.5(2) |
| C(11)—C(10)—C(9) | 121.4(3) |
| C(11)—C(10)—Se(1) | 121.2(2) |
| C(9)—C(10)—Se(1) | 117.4(2) |
| C(10)—C(11)—C(12) | 118.6(3) |
| C(10)—C(11)—H(11) | 119.9 |
| C(12)—C(11)—H(11) | 121.5 |
| C(13)—C(12)—C(11) | 120.9(3) |
| C(13)—C(12)—H(12) | 119.2 |
| C(11)—C(12)—H(12) | 119.9 |
| C(12)—C(13)—C(14) | 120.0(3) |
| C(12)—C(13)—H(13) | 120.2 |
| C(14)—C(13)—H(13) | 119.7 |
| C(9)—C(14)—C(13) | 119.8(3) |
| C(9)—C(14)—H(14) | 119.5 |
| C(13)—C(14)—H(14) | 120.7 |

Symmetry transformations used to generate equivalent atoms:
1 −x, −y + 2, −z + 1

TABLE 4

Anisotropic displacement parameters (Å² × 10³) for C₁₄H₁₃ClN₂O₃Se. The anisotropic displacement factor exponent takes the form:
$$-2\pi^2[h^2 a^{*2} U^{11} + \ldots + 2hka^*b^* U^{12}]$$

| Atom | U¹¹ | U²² | U³³ | U²³ | U¹³ | U¹² |
|---|---|---|---|---|---|---|
| Se(1) | 17(1) | 19(1) | 23(1) | −1(1) | −7(1) | −6(1) |
| Cl(1) | 24(1) | 23(1) | 26(1) | −2(1) | −9(1) | −4(1) |
| O(1) | 38(1) | 23(1) | 46(1) | 3(1) | −21(1) | −12(1) |
| O(2) | 20(1) | 20(1) | 41(1) | 0(1) | −12(1) | −7(1) |
| N(1) | 25(1) | 21(1) | 27(1) | −2(1) | −13(1) | −8(1) |
| N(2) | 21(1) | 23(1) | 39(1) | −1(1) | −11(1) | −7(1) |
| C(1) | 17(1) | 24(2) | 33(2) | −1(1) | −10(1) | −7(1) |
| C(2) | 20(1) | 24(2) | 25(1) | 1(1) | −6(1) | −7(1) |
| C(3) | 18(1) | 24(2) | 21(1) | −2(1) | −6(1) | −5(1) |
| C(4) | 31(2) | 32(2) | 27(2) | −4(1) | −10(1) | −12(1) |
| C(5) | 41(2) | 49(2) | 25(2) | −10(1) | −9(1) | −15(2) |
| C(6) | 34(2) | 50(2) | 22(2) | 4(1) | −9(1) | −16(2) |
| C(7) | 32(2) | 35(2) | 30(2) | 6(1) | −11(1) | −14(1) |
| C(8) | 20(1) | 21(1) | 24(1) | −1(1) | −6(1) | −8(1) |
| C(9) | 20(1) | 24(1) | 21(1) | −1(1) | −3(1) | −8(1) |
| C(10) | 17(1) | 20(1) | 21(1) | 0(1) | −6(1) | −6(1) |
| C(11) | 22(1) | 21(1) | 28(1) | 0(1) | −6(1) | −9(1) |
| C(12) | 21(1) | 30(2) | 35(2) | −2(1) | −7(1) | −11(1) |
| C(13) | 20(2) | 28(2) | 42(2) | −5(1) | −7(1) | −6(1) |
| C(14) | 19(1) | 23(2) | 38(2) | −4(1) | −7(1) | −5(1) |
| O(3A) | 184(10) | 108(6) | 170(7) | −20(5) | −43(8) | −22(6) |
| O(3B) | 184(10) | 108(6) | 170(7) | −20(5) | −43(8) | −22(6) |

TABLE 5

Hydrogen coordinates (×10⁴) and isotropic displacement parameters (Å² × 10³) for C₁₄H₁₃ClN₂O₃Se.

| Atom | x | y | z | U(eq) |
|---|---|---|---|---|
| H(1) | 2787 | 5575 | 9164 | 28 |
| H(2A) | 3733 | −1636 | 8115 | 32 |
| H(2B) | 5697 | −1951 | 8274 | 32 |
| H(4) | 2596 | 1971 | 6114 | 35 |
| H(5) | 2523 | 2987 | 4000 | 45 |
| H(6) | 2493 | 5403 | 3437 | 43 |
| H(7) | 2504 | 6894 | 4930 | 38 |
| H(11) | 5789 | 3949 | 8725 | 28 |
| H(12) | 8913 | 2395 | 8779 | 33 |
| H(13) | 9911 | −192 | 8642 | 37 |
| H(14) | 7825 | −1263 | 8399 | 32 |

TABLE 6

Torsion angles [°] for C₁₄H₁₃ClN₂O₃Se.

| | |
|---|---|
| N(1)—Se(1)—O(2)—C(8) | 63.7(5) |
| C(3)—Se(1)—O(2)—C(8) | 108.02(19) |
| C(10)—Se(1)—O(2)—C(8) | 5.77(18) |
| C(3)—Se(1)—N(1)—C(1) | 10.1(2) |
| C(10)—Se(1)—N(1)—C(1) | 111.1(2) |
| O(2)—Se(1)—N(1)—C(1) | 54.6(5) |
| Se(1)—N(1)—C(1)—O(1) | 169.1(2) |
| Se(1)—N(1)—C(1)—C(2) | −10.8(3) |
| O(1)—C(1)—C(2)—C(3) | −174.8(3) |
| N(1)—C(1)—C(2)—C(3) | 5.1(3) |
| O(1)—C(1)—C(2)—C(7) | 3.9(5) |
| N(1)—C(1)—C(2)—C(7) | −176.1(3) |
| C(7)—C(2)—C(3)—C(4) | −0.3(4) |
| C(1)—C(2)—C(3)—C(4) | 178.5(3) |
| C(7)—C(2)—C(3)—Se(1) | −176.5(2) |
| C(1)—C(2)—C(3)—Se(1) | 2.3(3) |
| N(1)—Se(1)—C(3)—C(2) | −6.4(2) |
| C(10)—Se(1)—C(3)—C(2) | −101.8(2) |
| O(2)—Se(1)—C(3)—C(2) | −178.9(2) |
| N(1)—Se(1)—C(3)—C(4) | 177.6(3) |
| C(10)—Se(1)—C(3)—C(4) | 82.3(3) |
| O(2)—Se(1)—C(3)—C(4) | 5.1(3) |
| C(2)—C(3)—C(4)—C(5) | −0.3(4) |

TABLE 6-continued

Torsion angles [°] for $C_{14}H_{13}ClN_2O_3Se$.

| | |
|---|---|
| Se(1)—C(3)—C(4)—C(5) | 175.2(2) |
| C(3)—C(4)—C(5)—C(6) | 0.2(5) |
| C(4)—C(5)—C(6)—C(7) | 0.5(5) |
| C(5)—C(6)—C(7)—C(2) | −1.1(5) |
| C(3)—C(2)—C(7)—C(6) | 1.0(4) |
| C(1)—C(2)—C(7)—C(6) | −177.7(3) |
| Se(1)—O(2)—C(8)—N(2) | 174.6(2) |
| Se(1)—O(2)—C(8)—C(9) | −5.6(3) |
| O(2)—C(8)—C(9)—C(14) | −176.6(3) |
| N(2)—C(8)—C(9)—C(14) | 3.2(4) |
| O(2)—C(8)—C(9)—C(10) | 2.3(4) |
| N(2)—C(8)—C(9)—C(10) | −177.9(2) |
| C(14)—C(9)—C(10)—C(11) | −0.9(4) |
| C(8)—C(9)—C(10)—C(11) | −179.8(2) |
| C(14)—C(9)—C(10)—Se(1) | −177.7(2) |
| C(8)—C(9)—C(10)—Se(1) | 3.4(3) |
| N(1)—Se(1)—C(10)—C(11) | 7.7(2) |
| C(3)—Se(1)—C(10)—C(11) | 93.8(2) |
| O(2)—Se(1)—C(10)—C(11) | 178.6(2) |
| N(1)—Se(1)—C(10)—C(9) | −175.5(2) |
| C(3)—Se(1)—C(10)—C(9) | −89.3(2) |
| O(2)—Se(1)—C(10)—C(9) | −4.62(19) |
| C(9)—C(10)—C(11)—C(12) | 1.1(4) |
| Se(1)—C(10)—C(11)—C(12) | 177.8(2) |
| C(10)—C(11)—C(12)—C(13) | −0.6(4) |
| C(11)—C(12)—C(13)—C(14) | −0.1(4) |
| C(10)—C(9)—C(14)—C(13) | 0.2(4) |
| C(8)—C(9)—C(14)—C(13) | 179.0(3) |
| C(12)—C(13)—C(14)—C(9) | 0.3(4) |

TABLE 7

Hydrogen bonds for $C_{14}H_{13}ClN_2O_3Se$ [Å and °].

| D-H...A | d(D-H) | d(H...A) | d(D...A) | <(DHA) |
|---|---|---|---|---|
| N(1)—H(1)...Cl(1)#2 | 0.88 | 2.59 | 3.097(2) | 117.5 |
| N(2)—H(2A)...O(1)#3 | 0.88 | 2.05 | 2.902(3) | 162.6 |
| N(2)—H(2B)...Cl(1)#4 | 0.88 | 2.36 | 3.194(2) | 159.0 |

Symmetry transformations used to generate equivalent atoms:
1 −x, −y + 2, −z + 1
2 x, y, z + 1
3 x, y − 1, z
4 −x + 1, −y, −z + 1

Example 8

Figure 5:
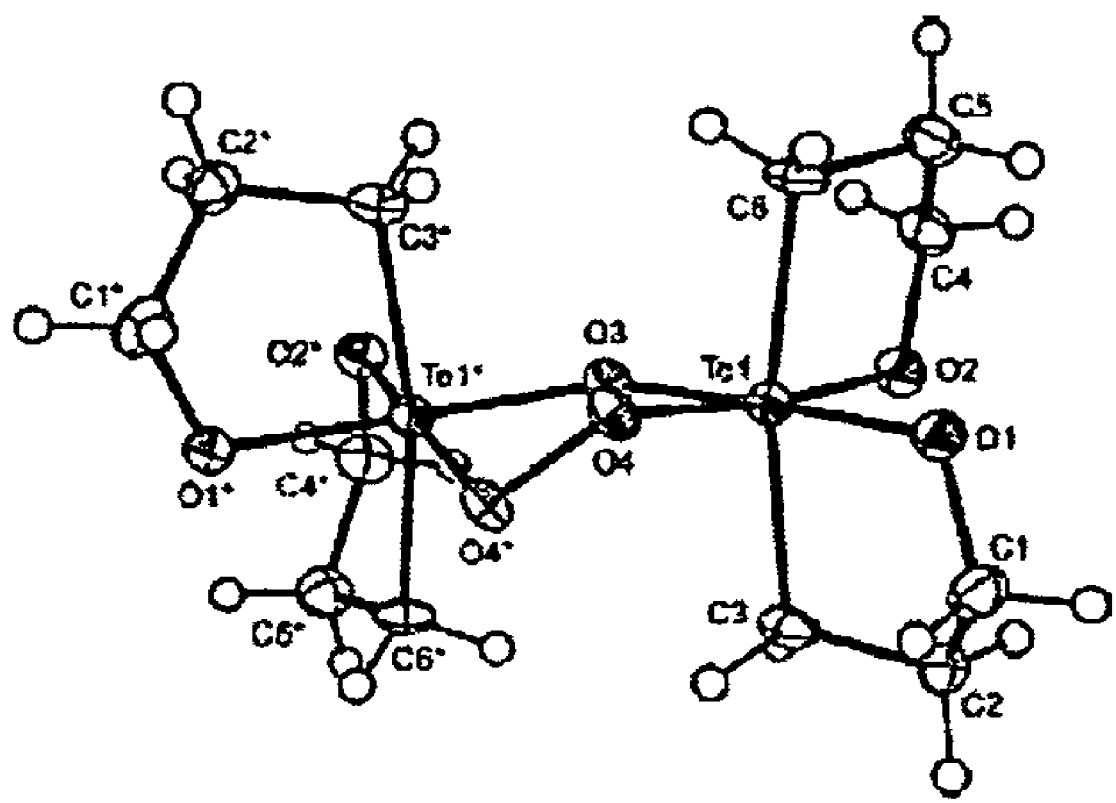
FIG. 5 is an X-ray crystal structure of compound 33.

Synthesis and X-Ray Crystallographic Data for 33 (FIG. 5)

Peroxide 33. Di(3-hydroxypropyl) telluride 28 (170 mg, 0.693 mmol) was dissolved in 15 mL of dichloromethane and treated with hydrogen peroxide (150 µL of 29% solution, 1.4 mmol). The mixture turned clear within ca. 1 min and was then stirred for additional 16 h at room temperature. The product was concentrated in vacuo to give 185 mg (100%) of a solid, which was recrystallized from ethanol to afford 126 mg (68%) of 33, mp 211-213° C.; IR (KBr) 1221, 1044, 989, 810 cm$^{-1}$; $^1$H NMR (300 MHz) δ 4.20-4.08 (m, 2H), 4.08-3.95 (m, 4H), 3.84-3.70 (m, 2H), 2.95-2.70 (m, 4H), 2.68-2.53 (m, 2H), 2.45-2.16 (m, 8H), 2.16-1.95 (m, 2H); $^{13}$C NMR (75 MHz) δ 61.2, 60.8, 37.9, 35.1, 24.7, 24.5; $^{125}$Te NMR (126 MHz) δ 1123.7. Analysis calcd for $C_{12}H_{24}O_7Te_2$: C, 26.91; H, 4.52. Found: C, 27.04; H, 4.37.

A colorless prismatic crystal of $C_{12}H_{24}O_7Te_2$ was coated with Paratone 8277 oil (Exxon) and mounted on a glass fiber. All measurements were made on a Nonius KappaCCD diffractometer with graphite monochromated Mo—Kα radiation. Cell constants obtained from the refinement Otwinowski, (Z. & Minor, W. (1997). "Processing of X-ray Diffraction Data Collected in Oscillation Mode", *Methods in Enzymology, Volume 276*: Macromolecular Crystallograpy, part A, p. 307-326, C. W. Carter, Jr. & R. M. Sweet, Eds., Academic Press) of 3421 reflections in the range 3.7<θ<27.5° corresponded to a centered monoclinic cell; details of crystal data and structure refinement have been provided in Table 8. The space group was uniquely determined from the systematic absences. The data were collected (Hooft, R. (1998). COLLECT: Users Manual, Nonius B. V., Delft. The Netherlands) at a temperature of 173(2) K. using the ω and φ scans to a maximum θ value of 27.5°. The data were corrected for Lorentz and polarization effects and for absorption using multi-scan method. Since the crystal did not show any sign of decay during data collection a decay correction was deemed unnecessary.

The structure was solved by the direct methods (Altomare, A., Cascarano, M., Giacovazzo, C. & Guagliardi, A. (1993) Completion and Refinement of Crystal Structures with SIR92. J. Appl. Cryst., 26, 343-350) and expanded using Fourier techniques (Altomare, A., Cascarano, M., Giacovazzo, C. & Guagliardi, A. (1993). Completion and Refinement of Crystal Structures with SIR92. J. Appl. Cryst., 26, 343-350). The non-hydrogen atoms were refined anisotropically. Hydrogen atoms were located from a difference map, were included at geometrically idealized positions and were not refined. The final cycle of full-matrix least-squares refinement using SHELXL97 (Sheldrick, G. M. (1997). SHELXL97—A Program for Refinement of Crystal Structures, University of Göttingen, Germany) converged (largest parameter shift was 0.00 times its esd) with unweighted and weighted agreement factors, R=0.055 and wR=0.147 (all data), respectively, and goodness of fit, S=1.16. The weighting scheme was based on counting statistics and the final difference map was essentially free of any chemically significant features with the largest residual electron density within 1.5 Å from the metal atom. The figure was plotted with the aid of ORTEPII (Johnson, C. K. (1976). ORTEPII. Report ORNL-5138. Oak Ridge National Laboratory, Tennessee, USA).

TABLE 8

Crystal data and structure refinement for $C_{12}H_{24}O_7Te_2$.

| | |
|---|---|
| Empirical formula | $C_{12}H_{24}O_7Te_2$ |
| Formula weight | 535.51 |
| Temperature | 173(2) K |
| Wavelength | 0.71073 Å |
| Crystal system | Monoclinic |
| Space group | C2/c |
| Unit cell dimensions | a = 20.345(9) Å α = 90°. |
| | b = 10.237(4) Å β = 107.27(2)°. |
| | c = 8.191(3) Å γ = 90°. |
| Volume | 1629.0(11) Å$^3$ |
| Z | 4 |
| Density (calculated) | 2.183 Mg/m$^3$ |
| Absorption coefficient | 3.61 mm$^{-1}$ |
| F(000) | 1024 |
| Crystal size | 0.10 × 0.06 × 0.04 mm$^3$ |
| Theta range for data collection | 3.7 to 27.5°. |
| Index ranges | −26 <= h <= 26, −13 <= k <= 12, −10 <= l <= 10 |
| Reflections collected | 3421 |
| Independent reflections | 1871 [R(int) = 0.037] |
| Completeness to theta = 27.5° | 99.4% |
| Absorption correction | Multi-scan method |
| Max. and min. transmission | 0.869 and 0.714 |
| Refinement method | Full-matrix least-squares on F$^2$ |
| Data/restraints/parameters | 1871/0/97 |

TABLE 8-continued

Crystal data and structure refinement for $C_{12}H_{24}O_7Te_2$.

| | |
|---|---|
| Goodness-of-fit on $F^2$ | 1.08 |
| Final R indices [I > 2sigma(I)] | R1 = 0.032, wR2 = 0.071 |
| R indices (all data) | R1 = 0.043, wR2 = 0.076 |
| Extinction coefficient | 0.00135(17) |
| Largest diff. peak and hole | 1.32 and −0.87 e.Å$^{-3}$ |

TABLE 9

Atomic coordinates ($\times 10^4$) and equivalent isotropic displacement parameters (Å$^2 \times 10^3$) for $C_{12}H_{24}O_7Te_2$. U(eq) is defined as one third of the trace of the orthogonalized $U^{ij}$ tensor.

| Atom | x | y | z | U(eq) |
|---|---|---|---|---|
| Te(1) | 811(1) | 2108(1) | 3924(1) | 16(1) |
| O(1) | 1599(2) | 1013(3) | 5249(4) | 23(1) |
| O(2) | 1298(2) | 3798(3) | 4531(4) | 22(1) |
| O(3) | 0 | 3052(4) | 2500 | 21(1) |
| O(4) | 209(2) | 485(3) | 3407(4) | 20(1) |
| C(1) | 2010(3) | 538(5) | 4227(6) | 27(1) |
| C(2) | 2001(2) | 1510(5) | 2802(6) | 23(1) |
| C(3) | 1260(3) | 1886(5) | 1906(6) | 22(1) |
| C(4) | 1169(3) | 4406(5) | 5972(6) | 26(1) |
| C(5) | 1066(3) | 3360(5) | 7240(6) | 27(1) |
| C(6) | 558(3) | 2346(5) | 6242(6) | 22(1) |

TABLE 10

Bond lengths [Å] and angles [°] for $C_{12}H_{24}O_7Te_2$.

| | |
|---|---|
| Te(1)—O(3) | 1.968(2) |
| Te(1)—O(2) | 1.983(3) |
| Te(1)—O(1) | 1.993(3) |
| Te(1)—O(4) | 2.032(3) |
| Te(1)—C(6) | 2.123(4) |
| Te(1)—C(3) | 2.125(4) |
| O(1)—C(1) | 1.433(5) |
| O(2)—C(4) | 1.426(5) |
| O(3)—Te(1)#1 | 1.968(2) |
| O(4)—O(4)#1 | 1.477(6) |
| C(1)—C(2) | 1.529(7) |
| C(2)—C(3) | 1.516(7) |
| C(4)—C(5) | 1.549(7) |
| C(5)—C(6) | 1.521(7) |
| O(3)—Te(1)—O(2) | 89.34(15) |
| O(3)—Te(1)—O(1) | 175.02(14) |
| O(2)—Te(1)—O(1) | 95.33(13) |
| O(3)—Te(1)—O(4) | 86.06(14) |
| O(2)—Te(1)—O(4) | 172.34(12) |
| O(1)—Te(1)—O(4) | 89.47(13) |
| O(3)—Te(1)—C(6) | 95.20(15) |
| O(2)—Te(1)—C(6) | 84.93(15) |
| O(1)—Te(1)—C(6) | 86.95(17) |
| O(4)—Te(1)—C(6) | 89.38(15) |
| O(3)—Te(1)—C(3) | 94.02(14) |
| O(2)—Te(1)—C(3) | 89.41(16) |
| O(1)—Te(1)—C(3) | 84.33(16) |
| O(4)—Te(1)—C(3) | 97.01(16) |
| C(6)—Te(1)—C(3) | 169.12(19) |
| C(1)—O(1)—Te(1) | 112.8(3) |
| C(4)—O(2)—Te(1) | 112.7(3) |
| Te(1)#1—O(3)—Te(1) | 121.2(2) |
| O(4)#1—O(4)—Te(1) | 109.95(15) |
| O(1)—C(1)—C(2) | 110.4(4) |
| C(3)—C(2)—C(1) | 108.6(4) |
| C(2)—C(3)—Te(1) | 104.2(3) |
| O(2)—C(4)—C(5) | 110.4(4) |
| C(6)—C(5)—C(4) | 108.5(4) |
| C(5)—C(6)—Te(1) | 104.6(3) |

Symmetry transformations used to generate equivalent atoms:
1 −x, y, −z + ½

TABLE 11

Anisotropic displacement parameters (Å$^2 \times 10^3$) for $C_{12}H_{24}O_7Te_2$. The anisotropic displacement factor exponent takes the form:
$-2\pi^2[h^2a^{*2}U^{11} + \ldots + 2 h k a^* b^* U^{12}]$

| Atom | $U^{11}$ | $U^{22}$ | $U^{33}$ | $U^{23}$ | $U^{13}$ | $U^{12}$ |
|---|---|---|---|---|---|---|
| Te(1) | 18(1) | 15(1) | 16(1) | 0(1) | 6(1) | −1(1) |
| O(1) | 21(2) | 28(2) | 19(2) | 2(1) | 7(1) | 3(1) |
| O(2) | 25(2) | 19(2) | 22(2) | −1(1) | 7(1) | −2(1) |
| O(3) | 24(2) | 18(2) | 22(2) | 0 | 5(2) | 0 |
| O(4) | 24(2) | 16(2) | 15(2) | 1(1) | 1(1) | −1(1) |
| C(1) | 22(2) | 26(3) | 34(3) | −4(2) | 11(2) | 2(2) |
| C(2) | 19(2) | 25(3) | 24(2) | −3(2) | 7(2) | −3(2) |
| C(3) | 31(3) | 22(2) | 16(2) | −2(2) | 11(2 ) | −4(2) |
| C(4) | 32(3) | 23(3) | 23(2) | −6(2) | 9(2) | −3(2) |
| C(5) | 31(3) | 31(3) | 20(2) | −5(2) | 8(2) | −4(2) |
| C(6) | 33(3) | 23(2) | 15(2) | −4(2) | 15(2) | −5(2) |

TABLE 12

Hydrogen coordinates (x $10^4$) and isotropic displacement parameters (Å$^2$ x $10^3$) for $C_{12}H_{24}O_7Te_2$.

| Atom | x | y | z | U(eq) |
|---|---|---|---|---|
| H(1A) | 1828 | −315 | 3719 | 32 |
| H(1B) | 2489 | 407 | 4955 | 32 |
| H(2A) | 2271 | 2297 | 3290 | 27 |
| H(2B) | 2210 | 1108 | 1975 | 27 |
| H(3A) | 1024 | 1193 | 1103 | 26 |
| H(3B) | 1238 | 2714 | 1267 | 26 |
| H(4A) | 751 | 4957 | 5585 | 31 |
| H(4B) | 1562 | 4976 | 6554 | 31 |
| H(5A) | 1511 | 2938 | 7829 | 33 |
| H(5B) | 886 | 3773 | 8114 | 33 |
| H(6A) | 78 | 2657 | 6014 | 26 |
| H(6B) | 610 | 1511 | 6879 | 26 |

TABLE 13

Torsion angles [°] for $C_{12}H_{24}O_7Te_2$.

| | |
|---|---|
| O(3)-Te(1)-O(1)-C(1) | 65.3(11) |
| O(2)-Te(1)-O(1)-C(1) | −94.5(3) |
| O(4)-Te(1)-O(1)-C(1) | 91.5(3) |
| C(6)-Te(1)-O(1)-C(1) | −179.1(3) |
| C(3)-Te(1)-O(1)-C(1) | −5.6(3) |
| O(3)-Te(1)-O(2)-C(4) | 87.1(3) |
| O(1)-Te(1)-O(2)-C(4) | −94.7(3) |
| O(4)-Te(1)-O(2)-C(4) | 34.0(10) |
| C(6)-Te(1)-O(2)-C(4) | −8.2(3) |
| C(3)-Te(1)-O(2)-C(4) | −178.9(3) |
| O(2)-Te(1)-O(3)-Te(1)#1 | 174.58(9) |
| O(1)-Te(1)-O(3)-Te(1)#1 | 14.7(10) |
| O(4)-Te(1)-O(3)-Te(1)#1 | −11.55(8) |
| C(6)-Te(1)-O(3)-Te(1)#1 | −100.57(13) |
| C(3)-Te(1)-O(3)-Te(1)#1 | 85.22(13) |
| O(3)-Te(1)-O(4)-O(4)#1 | 41.3(2) |
| O(2)-Te(1)-O(4)-O(4)#1 | 94.6(9) |
| O(1)-Te(1)-O(4)-O(4)#1 | −136.5(3) |
| C(6)-Te(1)-O(4)-O(4)#1 | 136.6(3) |
| C(3)-Te(1)-O(4)-O(4)#1 | −52.2(3) |
| Te(1)-O(1)-C(1)-C(2) | 30.9(5) |
| O(1)-C(1)-C(2)-C(3) | −49.0(5) |
| C(1)-C(2)-C(3)-Te(1) | 41.1(4) |
| O(3)-Te(1)-C(3)-C(2) | 164.5(3) |
| O(2)-Te(1)-C(3)-C(2) | 75.2(3) |
| O(1)-Te(1)-C(3)-C(2) | −20.2(3) |
| O(4)-Te(1)-C(3)-C(2) | −109.0(3) |
| C(6)-Te(1)-C(3)-C(2) | 16.6(11) |
| Te(1)-O(2)-C(4)-C(5) | 32.7(5) |
| O(2)-C(4)-C(5)-C(6) | −48.4(5) |
| C(4)-C(5)-C(6)-Te(1) | 38.6(5) |
| O(3)-Te(1)-C(6)-C(5) | −106.7(3) |
| O(2)-Te(1)-C(6)-C(5) | −17.8(3) |

TABLE 13-continued

Torsion angles [°] for $C_{12}H_{24}O_7Te_2$.

| | |
|---|---|
| O(1)-Te(1)-C(6)-C(5) | 77.8(3) |
| O(4)-Te(1)-C(6)-C(5) | 167.3(3) |
| C(3)-Te(1)-C(6)-C(5) | 41.1(11) |

Symmetry transformations used to generate equivalent atoms: #1 −x, y,−z+1/2

Example 9

Catalytic Activities of GPx Mimitics

Catalytic activity of some of the compounds synthesized as described the foregoing Examples are described in the tables below, where the activity measured is in terms of comparability to selenoenzyme glutathione peroxidase. Reactions were performed with BnSH (0.029 M), the catalyst (0.0029 M) and either 56% TBHP (0.038 M), 38% TBHP (0.023 M) or 29% $H_2O_2$(0.040 M) in $CH_2Cl_2$-MeOH (95:5) at 18° C., except for entries 7, 8, 17 and 18, where the solvent was $CH_2Cl_2$-MeOH (4:1).

Aromatic derivatives 19, 22, 24 and 25 proved inferior catalysts compared to the parent cyclic seleninate ester 14 and spirodioxyselenurane 16. In general, hydrogen peroxide was reduced faster than tert-butyl hydroperoxide in the presence of the selenium-based catalysts. The cyclic tellurinate ester 27 and spirodioxytellurane 29 proved to be superior catalysts to their selenium analogs 14 and 16, respectively, resulting in the fastest reaction rates.

2 BnSH + ROOH $\xrightarrow[\text{MeOH—CH}_2\text{Cl}_2]{\text{catalyst 10 mol \%}}$ BnSSBn + ROH + $H_2O$
at 18° C.

| Entry | Catalyst | $t_{1/2}$ (h) | Oxidant |
|---|---|---|---|
| 1 | 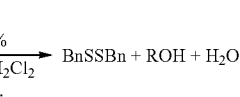 14 | 2.5 | 90% t-BuOOH[b] |
| 2 | | 90 | 56% t-BuOOH |
| 3 | | 167 | 38% t-BuOOH |
| 4 | | 18 | 29% $H_2O_2$ |
| 5 | 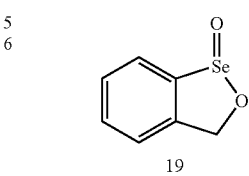 19 | 162 | 58% t-BuOOH |
| 6 | | 18 | 29% $H_2O_2$ |
| 7 | 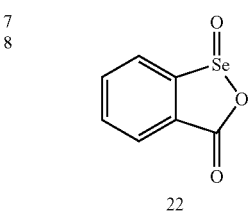 22 | 252 | 56% t-BuOOH |
| 8 | | 73 | 29% $H_2O_2$ |

-continued

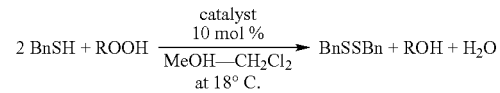

2 BnSH + ROOH $\xrightarrow[\text{MeOH—CH}_2\text{Cl}_2]{\text{catalyst 10 mol \%}}$ BnSSBn + ROH + $H_2O$
at 18° C.

| Entry | Catalyst | $t_{1/2}$ (h) | Oxidant |
|---|---|---|---|
| 9 | 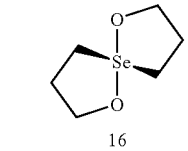 16 | 2.9 | 90% t-BuOOH[c] |
| 10 | | 1.9 | 56% t-BuOOH |
| 11 | | 2.1 | 38% t-BuOOH |
| 12 | | 0.2 | 29% $H_2O_2$ |
| 13 | 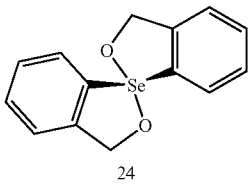 24 | 62 | 56% t-BuOOH |
| 14 | | 5.5 | 29% $H_2O_2$ |
| 15 | 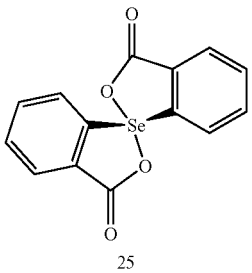 25 | 113 | 56% t-BuOOH |
| 16 | | 35 | 29% $H_2O_2$ |
| 17 |  27 | 0.05 | 56% t-BuOOH |
| 18 | | <0.05 | 29% $H_2O_2$ |
| 19 | 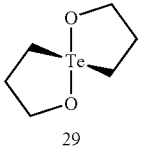 29 | 0.06 | 56% t-BuOOH |
| 20 | | 0.08 | 29% $H_2O_2$ |

[b] Data taken from Back, (i) Back, T. G.; Moussa, Z. J. Am. Chem. Soc. 2002, 124, 12104. (ii) Back, T. G.; Moussa, Z. J. Am. Chem. Soc. 2003, 125, 13455.
[c] Data taken from ref. Back, T. G.; Moussa, Z.; Parvez, M. Angew. Chem. Int. Ed. 2004, 43, 1268.

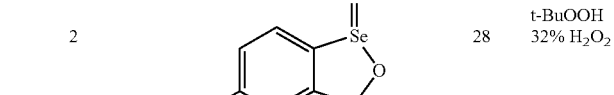

| Entry | Catalyst | $t_{1/2}$ (h) | Oxidant |
|---|---|---|---|
| 1 | 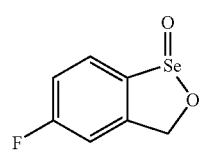 | 81 | 58% t-BuOOH |
| 2 | | 28 | 32% $H_2O_2$ |
| 3 | | 238 | 58% t-BuOOH |
| 4 | | 39 | 32% $H_2O_2$ |

-continued

| Entry | Catalyst | $t_{1/2}$ (h) | Oxidant |
|---|---|---|---|
| 5 | | 39 | 58% t-BuOOH |
| 6 | | 3.3 | 32% $H_2O_2$ |
| 7 | | 181 | 58% t-BuOOH |
| 8 | | 16 | 32% $H_2O_2$ |
| 9 | | 18 | 56% t-BuOOH |
| 10 | | 22 | 38% t-BuOOH |
| 11 | | 2.7 | 29% $H_2O_2$ |

While certain features have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:
1. A compound of formula 1:

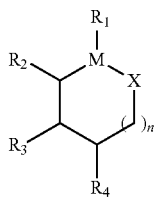

1 wherein,
the compound of formula 1 is a ring; and X is O or NH
M is Se or Te
n is 0 or 1
$R_1$ is:
oxygen and forms an oxo complex with M;
oxygen and forms together with the metal, a 4-7 membered ring, which optionally is substituted by an oxo or amino group; or
oxygen and forms together with the metal, a first 4-7 membered ring, which is optionally substituted by an oxo or amino group, wherein said first ring is fused with a second 4-7 membered ring, wherein said second 4-7 membered ring is optionally substituted by alkyl, alkoxy, nitro, aryl, cyano, hydroxy, amino, halogen, oxo, carboxy, thio, thioallcyl, or —NH(C=O)$R^A$, —C(=O)NR$^A$R$^B$, —NR$^A$R$^B$ or —SO$_2$R where $R^A$ and $R^B$ are independently H, alkyl or aryl;
$R_2$, $R_3$ and $R_4$ are independently hydrogen, alkyl, alkoxy, nitro, aryl, cyano, hydroxy, amino, halogen, carboxy, thio, thioalkyl, or —NH(C=O)$R^A$, —C(=O)NR$^A$R$^B$, —NR$^A$R$^B$ or —SO$_2$R where $R^A$ and $R^B$ are independently H, alkyl or aryl;
or $R_2$, $R_3$ or $R_4$ together, with the organometallic ring to which two of the substituents are attached, form a fused 4-7 membered ring system wherein said 4-7 membered ring is optionally substituted by alkyl, alkoxy, nitro, aryl, cyano, hydroxy, amino, halogen, oxo, carboxy, thio, thioallcyl, or —NH(C=O)$R^A$, —C(=O)NR$^A$R$^B$, —NR$^A$R$^B$ or —SO$_2$R where $R^A$ and $R^B$ are independently H, alkyl or aryl; wherein $R_4$ is not an alkyl;
wherein if $R_2$, $R_3$ and $R_4$ are hydrogens and $R_1$ forms an oxo complex with M, n is 0 then M is Te; or
if $R_2$, $R_3$ and $R_4$ are hydrogens and $R_1$ is an oxygen that forms together with the metal an unsubstituted, saturated, 5 membered ring, n is 0 then M is Te; or
if $R_1$ is an oxo group, and n is 0, $R_2$ and $R_3$ form together with the organometallic ring a fused benzene ring, $R_4$ is hydrogen, then M is Se; or
if $R_4$ is an oxo group, and $R_2$ and $R_3$ form together with the organometallic ring a fused benzene ring, $R_1$ is oxygen, n is 0 and forms together with the metal a first 5 membered ring, substituted by an oxo group a to $R_1$, and said ring is fused to a second benzene ring, then M is Te.

2. The compound of claim 1, represented by the compound of formula 2:

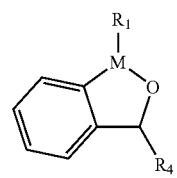

2 wherein, M, $R_1$ and $R_4$ are as described above.

3. The compound of claim 1, represented by the compound of formula 4:

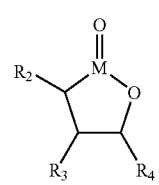

4 wherein, M, $R_2$, $R_3$ and $R_4$ are as described above.

4. The compound of claim 1, represented by the compound of formula 5:

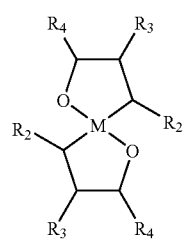

5 wherein, M, $R_2$, $R_3$ and $R_4$ are as described above.

5. The compound of claim 1, represented by the compounds:
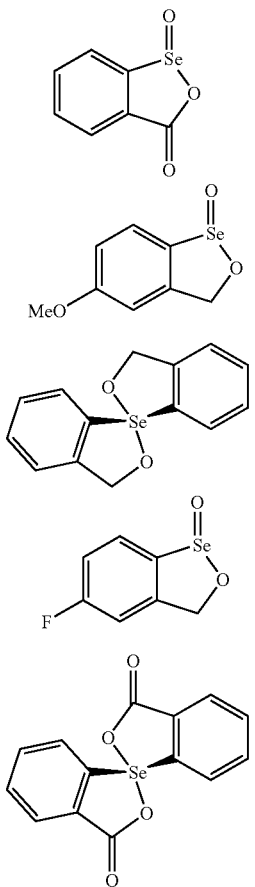
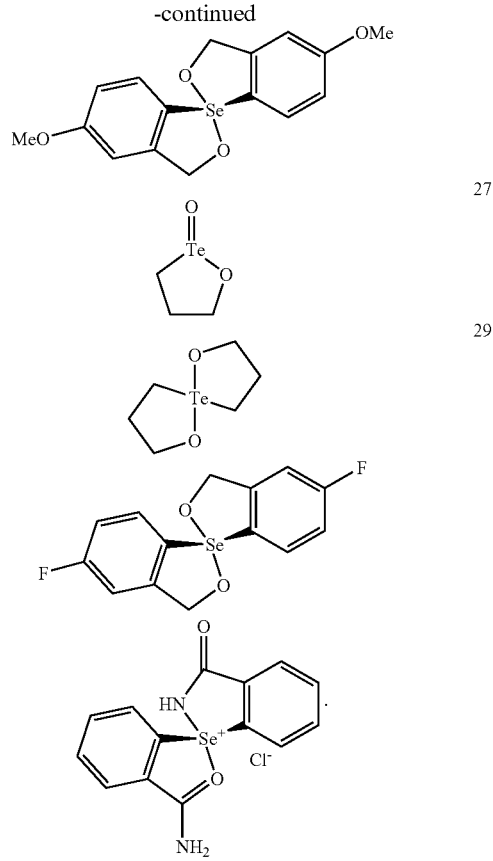
6. A composition comprising the compound of claim 1 and a suitable carrier or diluent.
* * * * *

UNITED STATES PATENT AND TRADEMARK OFFICE
CERTIFICATE OF CORRECTION

PATENT NO.       : 7,923,442 B2
APPLICATION NO.  : 11/543994
DATED            : April 12, 2011
INVENTOR(S)      : Dusan Kuzma et al.

It is certified that error appears in the above-identified patent and that said Letters Patent is hereby corrected as shown below:

In title page, item (75) Inventors, delete "Noah Berkowitz, New Rochelle, NY (US)".

In claim 1, column 44, line 24, delete "group a" and insert --group α-- therefor.

Signed and Sealed this
Third Day of April, 2012

David J. Kappos
*Director of the United States Patent and Trademark Office*